US010912751B2

(12) United States Patent
Newton et al.

(10) Patent No.: US 10,912,751 B2
(45) Date of Patent: Feb. 9, 2021

(54) FIXED DOSE COMBINATIONS AND FORMULATIONS COMPRISING ETC1002 AND EZETIMIBE AND METHODS OF TREATING OR REDUCING THE RISK OF CARDIOVASCULAR DISEASE

(71) Applicant: Esperion Therapeutics, Inc., Ann Arbor, MI (US)

(72) Inventors: Roger Schofield Newton, Ann Arbor, MI (US); Noah Laban Rosenberg, Livingston, NJ (US); Diane Elaine MacDougall, Lincoln, MA (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 0 days.

(21) Appl. No.: 15/558,084

(22) PCT Filed: Mar. 14, 2016

(86) PCT No.: PCT/US2016/022319
§ 371 (c)(1),
(2) Date: Sep. 13, 2017

(87) PCT Pub. No.: WO2016/149191
PCT Pub. Date: Sep. 22, 2016

(65) Prior Publication Data
US 2018/0064671 A1 Mar. 8, 2018

Related U.S. Application Data

(60) Provisional application No. 62/133,128, filed on Mar. 31, 2015, provisional application No. 62/250,921, filed on Nov. 4, 2015.

(51) Int. Cl.
*A61K 31/397* (2006.01)
*A61K 31/20* (2006.01)
*A61K 31/194* (2006.01)

(52) U.S. Cl.
CPC ............ *A61K 31/20* (2013.01); *A61K 31/194* (2013.01); *A61K 31/397* (2013.01)

(58) Field of Classification Search
CPC ..... A61K 31/20; A61K 31/194; A61K 31/397
See application file for complete search history.

(56) References Cited

U.S. PATENT DOCUMENTS

| 3,152,148 A | 10/1964 | Easterly et al. |
| 3,441,605 A | 4/1969 | Blake |
| 3,773,946 A | 11/1973 | Creger |
| 3,930,024 A | 12/1975 | Creger |
| 4,281,200 A | 7/1981 | Snoble |
| 4,287,200 A | 9/1981 | Kawamatsu et al. |
| 4,584,321 A | 4/1986 | Manghisi et al. |
| 4,613,593 A | 9/1986 | Yamatsu et al. |
| 4,634,119 A | 1/1987 | Pesthy |
| 4,634,719 A | 1/1987 | Takaishi et al. |
| 4,639,344 A | 1/1987 | Ueno et al. |
| 4,689,344 A | 8/1987 | Bar-Tana |
| 4,711,896 A | 12/1987 | Bar-Tana et al. |
| 4,714,762 A | 12/1987 | Hoefle et al. |
| 4,896,344 A | 1/1990 | Grady et al. |
| 5,166,174 A | 11/1992 | Ueno et al. |
| 5,225,439 A | 7/1993 | Ueno et al. |
| 5,284,858 A | 2/1994 | Ueno et al. |
| 5,380,709 A | 1/1995 | Ueno et al. |
| 5,428,062 A | 6/1995 | Ueno et al. |
| 5,502,198 A | 3/1996 | Picard et al. |
| 5,504,073 A | 4/1996 | Homan |
| 5,570,569 A | 11/1996 | Masuda |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Bisgaier et al. |
| 5,783,600 A | 7/1998 | Bisgaier et al. |
| 5,834,596 A | 11/1998 | Ageland et al. |
| 5,886,034 A | 3/1999 | Ueno et al. |
| 5,968,963 A | 10/1999 | Homan |
| 5,981,595 A | 11/1999 | Picard et al. |
| 6,004,925 A | 12/1999 | Dasseux et al. |
| 6,017,905 A | 1/2000 | Roark et al. |
| 6,037,323 A | 3/2000 | Dasseux et al. |
| 6,093,719 A | 7/2000 | Bocan |
| 6,093,744 A | 7/2000 | Lee et al. |

(Continued)

FOREIGN PATENT DOCUMENTS

| BR | PI0318046-8 A | 3/2019 |
| CA | 2513660 A1 | 5/2012 |

(Continued)

OTHER PUBLICATIONS

Remington, The Science and Practice of Pharmacy, Nineteenth Edition—1995, p. 710-712; pp. 1615-1617.*
Int'l Search Report, PCT/US2016/022319, dated Jun. 3, 2016, 2 pages.
Masuda et al., "Ezetimibe Improves Postprandial Hyperlipidaemia in Patients with Type IIb Hyperlipidaemia," Eur. J. Clin. Invest., vol. 39 (8), 2009, pp. 689-698.
Akdim et al., "Efficacy and Safety of Mipomersen, an Antisense Inhibitor of Apoliprotein B, in Hypercholesterolemic Subjects Receiving Stable Statin Therapy," J. Am. Coll. Cardiol., vol. 55, Apr. 13, 2010, pp. 1611-1618.
Norata et al., "New Therapeutic Principles in Dyslipidaemia: Focus on LDL and Lp(a) Lowering Drugs," Eur. Heart J., vol. 34(24); Mar. 18, 2013, pp. 1783-1789a.

(Continued)

*Primary Examiner* — Shobha Kantamneni
(74) *Attorney, Agent, or Firm* — Goodwin Procter LLP

(57) ABSTRACT

Disclosed herein are compositions comprising fixed doses of ETC-1002 and Ezetimibe. Also disclosed herein are methods for using fixed doses of ETC-1002 and Ezetimibe. Uses include methods of treating cardiovascular disease or reducing the risk of cardiovascular disease in a subject. Uses also include methods of treating hypercholesterolemia in a subject.

13 Claims, 3 Drawing Sheets

(56) References Cited

U.S. PATENT DOCUMENTS

| | | |
|---|---|---|
| 6,124,309 A | 9/2000 | Bocan |
| 6,143,755 A | 11/2000 | Bocan |
| 6,207,822 B1 | 3/2001 | Thiruvengadam et al. |
| 6,362,236 B1 | 3/2002 | Aviram et al. |
| RE37,721 E | 5/2002 | Rosenblum et al. |
| 6,410,802 B1 | 6/2002 | Dasseux et al. |
| 6,459,003 B1 | 10/2002 | Dasseux et al. |
| 6,506,799 B1 | 1/2003 | Dasseux |
| 6,646,170 B2 | 11/2003 | Dasseux et al. |
| 6,673,780 B2 | 1/2004 | Dasseux et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |
| 6,790,953 B2 | 9/2004 | Dasseux et al. |
| 6,831,105 B2 | 12/2004 | Dasseux |
| 6,909,014 B2 | 6/2005 | Dasseux et al. |
| 7,053,080 B2 | 5/2006 | Davis et al. |
| 7,119,221 B2 | 10/2006 | Dasseux et al. |
| 7,192,940 B2 | 3/2007 | Dasseux et al. |
| 7,304,093 B2 | 12/2007 | Dasseux et al. |
| 7,335,799 B2 | 2/2008 | Dasseux et al. |
| 7,405,226 B2 | 7/2008 | Dasseux et al. |
| 7,576,130 B2 | 8/2009 | Dasseux et al. |
| 7,705,177 B2 | 4/2010 | Oniciu et al. |
| 7,812,199 B2 | 10/2010 | Dasseux et al. |
| 7,838,554 B2 | 11/2010 | Dasseux et al. |
| RE42,461 E | 6/2011 | Rosenblum et al. |
| 8,067,466 B2 | 11/2011 | Dasseux et al. |
| 8,084,498 B2 | 12/2011 | Dasseux et al. |
| 8,153,690 B2 | 4/2012 | Dasseux et al. |
| 8,309,604 B2 | 11/2012 | Dasseux et al. |
| 8,497,301 B2 | 7/2013 | Dasseux et al. |
| 8,623,915 B2 | 1/2014 | Dasseux et al. |
| 8,642,653 B2 | 2/2014 | Dasseux et al. |
| 8,975,300 B2 | 3/2015 | Dasseux et al. |
| 9,000,041 B2 | 4/2015 | Dasseux et al. |
| 9,006,290 B2 | 4/2015 | Dasseux et al. |
| 9,452,964 B2 | 9/2016 | Dasseux et al. |
| 9,624,152 B2 | 4/2017 | Dasseux et al. |
| 10,047,028 B2 | 8/2018 | Dasseux et al. |
| 10,118,881 B2 | 11/2018 | Dasseux et al. |
| 2003/0180352 A1 | 9/2003 | Patel et al. |
| 2004/0214777 A1 | 10/2004 | McGrath |
| 2004/0214887 A1 | 10/2004 | Dasseux et al. |
| 2005/0043278 A1 | 2/2005 | Dasseux et al. |
| 2005/0119333 A1 | 6/2005 | Dasseux |
| 2005/0214887 A1 | 9/2005 | Emori et al. |
| 2007/0155704 A1 | 7/2007 | Dasseux et al. |
| 2007/0179120 A1 | 8/2007 | Dasseux et al. |
| 2008/0249166 A1 | 10/2008 | Dasseux et al. |
| 2009/0024789 A1 | 1/2009 | Rajan et al. |
| 2009/0247489 A1 | 10/2009 | Dasseux et al. |
| 2010/0291207 A1 | 11/2010 | Gat et al. |
| 2010/0297105 A1 | 11/2010 | Geary et al. |
| 2011/0262497 A1 | 10/2011 | Injac et al. |
| 2012/0129930 A1 | 5/2012 | Dasseux et al. |
| 2012/0135976 A1 | 5/2012 | Kerc et al. |
| 2012/0225908 A1 | 9/2012 | Dasseux et al. |
| 2013/0190354 A1 | 7/2013 | Wen et al. |
| 2013/0280176 A1 | 10/2013 | Diezi et al. |
| 2013/0302399 A1 | 11/2013 | Feldhaus et al. |
| 2014/0093564 A1 | 4/2014 | Bradley et al. |
| 2015/0005386 A1 | 1/2015 | Bisgaier |
| 2015/0344388 A1 | 12/2015 | Dasseux et al. |
| 2017/0349516 A1 | 12/2017 | Dasseux et al. |
| 2019/0084908 A1 | 3/2019 | Dasseux et al. |

FOREIGN PATENT DOCUMENTS

| | | |
|---|---|---|
| CN | 107530308 A | 1/2018 |
| EP | 0284108 A2 | 9/1988 |
| EP | 0720599 A1 | 7/1996 |
| EP | 10417421 A2 | 11/2000 |
| EP | 1137634 A1 | 10/2001 |
| EP | 1597223 A2 | 2/2017 |
| EP | 2404890 A1 | 7/2017 |
| EP | 3270909 A1 | 1/2018 |
| FR | 1545224 A | 11/1968 |
| GB | 1196594 A | 7/1970 |
| GB | 1196595 A | 7/1970 |
| GB | 1196596 A | 7/1970 |
| GB | 1196597 A | 7/1970 |
| GB | 1196598 A | 7/1970 |
| IN | 201717035904 | 12/2017 |
| JP | 4931349 B2 | 2/2012 |
| MX | 263623 | 1/2008 |
| MX | 349134 B | 7/2017 |
| WO | WO-1996030328 A1 | 10/1996 |
| WO | WO-1998030530 A1 | 7/1998 |
| WO | WO-1999000116 A2 | 1/1999 |
| WO | WO 99/26583 A2 | 6/1999 |
| WO | WO-2002030860 A1 | 4/2002 |
| WO | WO 2005/062897 A2 | 7/2005 |
| WO | WO-2005068412 A1 | 7/2005 |
| WO | WO-2005109170 A2 | 11/2005 |
| WO | WO 07/058335 A1 | 5/2007 |
| WO | WO-2012040177 A1 | 3/2012 |
| WO | WO 2014/099584 A1 | 6/2014 |
| WO | WO 2016/149191 A1 | 9/2016 |
| WO | WO 2016/149405 A1 | 9/2016 |

OTHER PUBLICATIONS

Esperion Therapeutics, "Esperion Therapeutics Announces Positive Top-Line Phase 2b Results for ETC-1002, an Investigational Therapy for Patients With Hypercholesterolemia," Esperion Press Release, Oct. 1, 2014, entire document.

European Extended Search Report, European Application No. 16765682. 6, dated Jun. 28, 2018, 10 pages.

Anonymous: "NCT02072161: Evaluation of ETC-1002 vs Placebo in Patients Receiving Ongoing Statin Therapy," Clinicaltrials.gov, Apr. 3, 2014, pp. 1-9, [Online] [Retrieved on Jun. 20, 2018] Retrieved from the Internet<URL:https://clinicaltrials.gov/ct2/history/NCT02072161?V_2=View#StudyPage Top>.

Ballantyne, C. et al., "Abstract 17499: ETC-1002 Incrementally Lowers Low Density Lipoprotein-Cholesterol in Patients with Hypercholesterolemia Receiving Stable Statin Therapy," Circulation, Nov. 6, 2015, p. 1, vol. 132, No. Suppl. 3.

Ballantyne, C. et al., "Effect of ETC-1002 on Serum Low-Density Lipoprotein Cholesterol in Hypercholesterolemic Patients Receiving Statin Therapy," American Journal of Cardiology, Apr. 6, 2016, pp. 1928-1933, vol. 117, No. 12.

Ballantyne, C. et al., "Efficacy and Safety of a Novel Dual Modulator of Adenosine Triphosphate-Citrate Lyase and Adenosine Monophosphate-Activated Protein Kinase in Patients with Hypercholesterolemia," Journal of the American College of Cardiology, Sep. 24, 2013, pp. 1154-1162, vol. 62, No. 13.

Gutierrez, M. J. et al., "Efficacy and Safety of ETC-1002, a Novel Investigational Low-Density Lipoprotein-Cholesterol-Lowering Therapy for the Treatment of Patients with Hypercholesterolemia and Type 2 Diabetes Mellitus," Arteriosclerosis Thrombosis and Vascular Biology, Mar. 2014, pp. 676-683, vol. 34, No. 3.

Nikolic, D. et al., "ETC-1002: A Future Option for Lipid Disorders?" Atherosclerosis, Elsevier, Dec. 2014, pp. 705-710, vol. 237, No. 2.

PCT Written Opinion, PCT Application No. PCT/US2016/022319, dated Jun. 3, 2016, 8 pages.

PCT International Search Report and Written Opinion, PCT Application No. PCT/US2016/022694, dated May 31, 2016, 12 pages.

United States Securities and Exchange Commission Form 10-Q, Esperion Therapeutics, Inc., Filed Nov. 6, 2013 for the Period Ending Sep. 30, 2013, 54 pages.

Berenson, A., "For Widely Used Drug, Question of Usefulness is Still Lingering," The New York Times Company, Sep. 1, 2008, © 2018, 12 pages, [Online] [Retrieved Jan. 25, 2018] Retrieved from the Internet<URL: http://www.nytimes.com/2008/09/02/business/02vytorin.html>.

Kolata, G., "Dashing Hopes, Study Shows a Cholesterol Drug Had No Effect on Heart Health," The New York Times Company, Apr.

(56) References Cited

OTHER PUBLICATIONS 3, 2016, © 2018, 9 pages, [Online] [Retrieved Jan. 25, 2018] Retrieved from the Internet<URL: https://www.nytimes.com/2016/04/04/health/dashing-hopes-study-shows-cholesterol-drug-has-no-benefits.html>.
Asclepia Capital: Clarifying the Conversation Part II: Esperion Therapeutics, INc. (ESPR), Sep. 7, 2015, 9 pages.
Pinkosky, S.L. et al., "Liver-Specific ATP-Citrate Lyase Inhibition by Bempedoic Acid Decreases LDL-C and Attenuates Atherosclerosis," Nature Communications, Nov. 28, 2016, pp. 1-13.
U.S. Appl. No. 15/859,279, filed Dec. 29, 2017, Inventors: Mohamed Abdelnasser et al. [Copy Not Enclosed].
U.S. Appl. No. 62/456,571, filed Feb. 8, 2017, Inventors: Narendra Lalwani et al. [Copy Not Enclosed].
Pinkosky, S.L. et al., "AMP-Activated Protein Kinase and ATP-Citrate Lyase are Two Distinct Molecular Targets for ETC-1002, a Novel Small Molecule Regulator of Lipid and Carbohydrate Metabolism," Journal of Lipid Research, 2013, pp. 134-151, vol. 54.
European Extended Search Report, European Application No. 16765550.5, dated Oct. 8, 2018, 8 pages.
Gagné, C. et al., "Efficacy and Safety of Ezetimibe Monotherapy in 6-10 Year Old Children with Heterozygous Familial or Nonfamilial Hypercholesterolemia," Journal of Clinical Lipidology, Jan. 1, 2013, pp. 257-258, [Online] [Retrieved on Sep. 25, 2018] Retrieved from the Internet<URL:https://www.lipidjournal.com/article/S1933-2874(13)00108-6/pdf>.
Chilean Office Action, Chilean Application No. 2299-2017, dated Nov. 13, 2018, 12 pages.
Chilean Office Action, Chilean Application No. 2334-2017, dated Nov. 13, 2018, 15 pages.
Ackerly, et al., 1995, "A novel approach to dual-acting thromboxane receptor antagonist/synthase inhibitors based on the link of 1.3-dioxane-thrombaxane receptor antagonists and -thromboxane synthase inhibitors", J. Med. Chem. 38:1608-1628.
Acton, et al., 1996, "Identification of scavenger receptor SR-B1 as high density lipoprotein receptor", Science. 271(5248):518-20.
Ahrens, et al., 1967, "A direct method for preparing pyridoxal and 4-pyridoxic acid (1)", J. Heterocyl. Chem. 4:625-26.
Alexander, K., et al., 1948, "4.4-Dichlorodibutyl ether and its derivatives from tetrahydrofuran", J. Am. Chem. Soc. 70:1839-42.
Ansels, Pharmaceutical Dosage Forms and Drug Delivery Systems, 7th Ed. 1999, Lippincott, Williams and Wilkins; Chapters 3 and 7; pp. 60-100 and 179-228.
Aulton et al., Aulton's Pharmaceutics: The Design and Manufacture of Medicines, 4th Edition, Edited by Michael E. Aulton and Kevin M.G. Taylor, 2013, Churchill Livingstone Elsevier, Chapter 12.
Badimon, et al., 1992, "Role of High density lipoproteins in the regression of atherosclerosis", Circulation 85 (Suppl);11186-94.
Bailey, et al. "Convenient general method for the preparation of primary alkyllithiums by lithium-iodine exchange," (1990) J. Org. Chem. vol. 55, No. 19, pp. 5404-5406.
Barrans, et al., 1996, "Pre-beta HDL; structure and metabolism", Biochim, Biophys. Acta. 1300(2):73-85.
Becker, et al., 1982, "Intramolecular photoaddition of terminal allenes to conjugated cyclohexenones", J. Org. Chem. 47:3297-3310.
Beilstein Report for Compound Beilstein Registry No. 1741087, based in part on Crisan et al. (1956), Ann. Chim, (Paris), 13(1): 436-459.
Beilstein Report for Compound Beilstein Registry No. 1778991, based in part on Pechmann (1904), Chem. Ber., 37: 3819.
Beilstein Report for Compound Beilstein Registry No. 1784568, based in part on English (1941), J. Am. Chem. Soc., 63 (4): 941-943.
Beilstein Report for Compound Beilstein Registry No. 2961112, based in part on Lardelli et al. (1967), Recl. Trav. Chim., 86: 481-503.
Beilstein Report for Compound Beilstein Registry No. 5836264, based in part on Weber et al. (1992), J. Med. Chem., 35(21): 3755-3773.
Beilstein Report for Compound Beilstein Registry No. 7473723, based in part on Rieke et al. (1996), J. Org. Chem., 61(8): 2726-2730.
Beilstein Report for Compound, Beilstein Registry No. 5815199 based in part on Weber et al. (1992), J. Med. Chem., 35(21): 3755-3773.
Bernady, et al. "Prostaglandins and congeners. 20. Synthesis of prostaglandins via conjugate addition of lithium trans-1-alkenyltrialkylalanate reagents. A novel reagent for conjugate 1,4-additions," J. Org. Chem. (1979) vol. 44, No. 9, pp. 1438-1447.
Bhanot, et al. "Synthetic studies on Terpenoids. 5. Syntheses of γ- and δ-Lactones from β-(2,7-Dimethyl-1,2-dihdroxycycloheptyl)propionic Acid," J. Org. Chem. (1977) vol. 42, pp. 1623-1627.
Bicking, et al., "11,12-Secoprostaglandins. 1. Acylhydroxyalkanoic acids and related compounds", J. Med. Chem., 1977, pp. 35-43, vol. 20.
Bisgaier, et al., 1997, "Attenuation of plasma low density lipoprotein cholesterol by select 3-hydroxy-3-methylglutaryl coenzyme A reductase inhibitors in mice of low density lipoprotein receptors", J. Lipid Res. 38 (12):2502-2515.
Bisgaier, et al., 1998, "A novel compound that elevates high density lipoprotein and activates the peroxisome proliferator activated receptor", J. Lipid Res. 39(1):17-30.
Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.
Blatt, et al., "The reducing action of Grignard reagent and the synthesis of tertiary aliphatic carbinols", J. Org. Chem., 1932, pp. 1495-1499, vol. 54.
Bohme, V. and Lener, W., 1955, Annalen der Chemie, 595;169-178 (Non-English Copy).
Bongini, et al., 1979 "A simple and practical method for tetrahydropyranylation of alcohols and phenols", Synthesis 618-620.
Brown, et al. "Selective reductions. 26. Lithuim triethylborohydride as an exceptionally powerful and selective reducing agent in organic synthesis. Exploration of the reactions with selected organic compounds containing representative functional groups," J. Org. Chem. (1980) vol. 45, No. 1, pp. 1-12.
Brown, H. C. et al. "Hydroboration. 67. Cyclic hydroboration of acyclic alpha,omega-dienes with 9-borabicyclo[3.3.1]nonane/borane-dimethyl sulfide," J. Org. Chem. (1984) vol. 49, No. 6, pp. 1072-1078.
Brown, H. C. et al. "Selective reductions. VII. Reaction of lithium trimethoxyaluminohydride with selected organic compounds containing representative functional groups," J. Am. Chem. Soc. (1965) vol. 87, No. 24, pp. 5614-5620.
Bruce, et al., 1998, "Plasma lipid transfer proteins, high-density lipoproteins, and reverse cholesterol transport", Annu Rev Nutr. 1998;18:297-330.
Compagna, et al., 1994, "Cyclic Amidine Analogues of Taurine and Homotaurine; Synthesis and Effects on Rat Skeletal Muscle", Farmaco, Ed. Sci 49:653-658.
Carothers, 1924, "Platinum oxide as a catalyst in the reduction of organic compounds. V. The preparation of primary alcohols by the catalytic hydrogenation of aldehydes," J. Am. Chem. Soc. 46:1675-83.
Cerny, et al., 1969, "Properties of Sodium Bis-(2-Methoxyethoxy)-Aluminum Hydride", Collect Czech Chem Comm. 34:1025-33.
Chadwick, et al., 1979, "Reaction between N-Alkylpyroles and Alkyllithium Reagents" J. Chem Soc., Perkin Trans. 12845.
Chaikin, et al., 1949, "Lithium Borohydride as a Reducing Agent", J. Am. Chem. Soc. 71:3245-48.
Chen, et al., 1998, "Asymmetric total synthesis of phosphatidylinositol 3-phosphate and 4-phosphate derivatives", J. Org. Chem. 63:6511-22.
Comins, et al., 1981, "A one pot synthesis of unsymmetrical secondary alcohols from two grignard reagents", Tetrahedron Lett. 22:1085-88.
Corbridge, 1985, "Phosphorus: An Outline of its Chemistry, Biochemistry and Technology", Studies in Inorganic Chemistry, 3rd ed, pp. 357-395.

(56) References Cited

OTHER PUBLICATIONS

Corey, et al., 1967, "A useful method for the conversion of alcohols into iodides", J. Org. Chem. 32:4160-4161.
Corey, et al., 1979, "Useful procedures for the oxidation of alcohols involving pyridinum dichromate in aprotic media", Tetrahedron Lett. 5:399-402.
Dalton, J.C. et al. (1971) "Type I and Type II Photochemical Reactions of Some Five- and Six-Membered Cycloalkanones," J. Am. Chem. Soc., 93 (26): 7213-21.
Danheiser, et al., 1991, "A Practical and Efficient Method for Synthesis of β-Lactones", J. Org. Chem. 58:1176-65.
Dansky HM, Fisher Ea, 1999, "High-density lipoprotein and plaque regression: the good cholesterol gets even better", Circulation 100(17): 1762-3.
Decossin, et al., 1997, "Subclasses of LpA-I in coronary artery disease: distribution and cholesterol efflux ability", Eur J Clin Invest. 27(4):299-307.
De Sarlo, et al., 1971, "Isoxazolin-5-one", J. Chem Soc. 88-89.
Eaton, et al., 1972, "Hydroxypropylation", J. Org. Chem. 37:1947-50.
Ehlinger, et al., 1980, "Silicon in Synthesis. 10. The (trimethylsiyl)allyl Anion: A. beta-Acyl anion equivalent for the conversion of aldehydes and ketones into gamma-lactone", J. Am. Chem. Soc. 102:5004-11.
Eisch, et al. 1978, "Synthesis of lactones via the titanium-catalyzed hydromagnesiation of alkenols", J. Organomet. Chem. 160:C8-C12.
Fielding & Fielding, 1995, "Molecular physiology of reverse cholesterol transport", J. Lipid Res. 36(2):211-28.
Fraser, et al., 1985, "Acidity measurements in THF. V. Heteroaromatic compounds containing 5-membered rings", Can J. Chem. 63:3505-09.
Gagné, et al. "Efficacy and Safety of Ezetimibe Monotherapy in 6-10 Year Old Children with Heterozygous Familial or Non-familial Hypercholesterolemia" Journal of Clinical Lipidology, Jan. 1, 2013; pp. 257-258.
Garegg, et al., 1980, "Novel Reagent System for converting a Hydroxy-group into an Iodo-group in carbohydrates with inversion of Configuration", J.C.S. Perkin I 2866-2868.
Gearing, et al., 1993, "Interaction of the peroxisome-proliferator-activated receptor and retinoid X receptor", Proc. Natl. Acad. Sci. USA 90(4):14440-1444.
Gigg, et al., 1967, "The Preparation of Unsymmetrical Diglycerides", J. Chem. Soc., C. 431-434.
Gleiter, R. et al. "Synthesis and properties of 4,4,9,9-tetramethyl-1-oxa-cycloundecane-5,6,7,8-tetrone and 5,5,10,10-tetramethyl-1-oxa-cyclotridecane-6,7,8,9-tetrone," Chemistry—A European Journal (1996) vol. 2, No. 3, pp. 271-277.
Gleiter, R. et al., "Synthesis of 5,5,10,10-tetramethyl-1-oxacyclotridecane-6,7,8,9-tetrone—on the mechanism of the Rubotom reaction," Eur. J. Org. Chem. (1995) No. 9, pp. 1655-1661.
Green and Kehinde, 1975, "An established predispose cell line and its differentiation in culture II. Factors affecting the adipose conversion", Cell. 5(1):19-27.
Greene, T.W., 1999, "Protection for the Hydroxyl Group, Including 1,2-and 1,3-Diols", Protective Groups in Organic Synthesis.
Harris and Kletzien, 1994, "Localization of pioglitazone response element in the adipocyte fatty acid-binding protein gene", Mol Pharmacol. 45(3):439-45.
Hayden and Ma, 1992, "Molecular genetics of human lipoprotein lipase deficiency", Mol Cell Biochem. 113(2):171-6.
Heyman, et al., 1992, "9-cis retinoic acid is high affinity ligand for the retinoid X receptor", Cell 68(2):397-406.
Hidaka and Fidge, 1992, "Affinity purification of the hepatic high-density lipoprotein receptor identifies two acidic glycoproteins and enables further characterization of their binding properties", Biochem. J. 15(Pt1):161-7.
Hirano, et al., 1997, "Genetic cholesteryl ester transfer deficiency is extremely frequent in the Omagari area of Japan. Marked hyperalphalipoproteinema caused by CETP gene mutation is not associated with longevity", Arterioscler. Thromb. Vasc.Biol. 17(6):1053-1059.
Hoyer, et al., 1986, "Catalysis by acidic clay of the protective tetrahydropyranylation of alcohols and phenols", Synthesis 655-57.
Hudlicky, M., 1996, "Reduction of aldehydes and their derivatives", Reductions in Organic Chemistry, 2nd ed. pp. 137-139.
Hudlicky, M., 1996, "Reduction of esters and lactones of carboxylic acids", Reduction in Organic Chemistry 2nd ed. pp. 212-217.
International Search Report and the Written Opinion of the International Search Authority, or the Declaration, Int'l Application No. PCT/US18/17434, dated Apr. 19, 2018, 16 pages.
International Search Report, International Application No. PCT/US2003/041411, dated Dec. 8, 2004 (12 pages).
Ishibashi, et al., 1993, "Hypercholesterolemia in low density lipoprotein receptor knockout mice and its reversal by adenovirus-mediated gene delivery", J. Clin. Invest. 92(2):883-93.
Ishibashi, et al., 1994, "Massive xanthomatosis and atherosclerosis in cholesterol-fed low density lipoprotein receptor-negative mice", J. Clin Invest. 93(5):1885-93.
Isseman and Green, 1990, "Activation of a member of the steroid hormone receptor superfamily by peroxisome proliferators", Nature 347(6294):645-650.
Iwai, et al, 1966, "Studies on acetylenic compounds. Xliv. Synthesis of 3-aminoisoxazoles and 3hydroxyisoxazoles (3-lsoxazolones)", Chem. Pharm. Bull. 14:1277-88.
Jetter, R., "Long-chain alkanediols from Myricaria germanica leaf cuticular waxes," Phytochemistry, 55 (2), 2000, pp. 169-176.
Johnston, et al., 1988, "A new, mild heterogeneous catalyst for the tetrahydropyranylation of alcohols and phenols", Synthesis 393-4.
Katritzky, et al., 1993, "Generation and Reactions of sp2-Carbanionic Centers in the Vicinity of Heterocyclic Nitrogen Atoms", Adv. Het. Chem. 56:155-303.
Katsiki et al., "Non-alcoholic Fatty Liver Disease and Dyslipidemia: an Update," 2016, Metabolism, 65(8), pp. 1109-1123.
Keller and Wahli, 1993, "Peroxisome proliferator-activated receptors-A link between endocrinology and Nurition?" Tem, 4:291-295.
Keller, et al., 1993, "Fatty acids and retinoids control lipid metabolism through activation of peroxisome proliferator-activated receptor-retinoid X receptor heterodimers", Proc. Natl. Acad. Sci. Usa 90(6):2160-2164.
Kessar, et al., 1997, "Lewis acid complexation of tertiary amines and related compounds: a strategy for a a-deprotonation and stereocontrol", Chem. Rev. 97:721-37.
Kletzein, et al., 1991, "Enhancement of adipocyte differentiation by an insulin-sensitizing agent", Mol Pharmacol 41(2):393-398.
Kliewer, et al., 1992, "Convergence of 9-cis retinoic acid and peroxisome proliferator signaling pathways through heterodimer formation of their receptors", Nature 27;358(6389):771-4.
Kurata, et al., 1998, "A candidate high density lipoprotein (HDL) receptor, HB2, with possible multiple functions shows sequence homology with adhesion molecules", J. Atherosclerosis and Thrombosis 4(3):112-7.
Kurz, et al., 1985, "Anomalous selectivities in methyl transfers to water: An explanation using free energy surfaces which model the effects of non-equilibrium solvation", Isr. J. Chem. 26:339-48.
Kurz, et al.. "Evidence for rate-determining solvation change in methyl transfer to water. Solvent dependence of H2O/D2O kinetic isotope effects," J. Am. Chem. Soc. (1986) vol. 108, pp. 2960-2968.
Lagrost, et al., 1996, "Opposite effects of cholesteryl ester transfer protein and phospholipid transfer protein on the size distribution of plasma high density lipoproteins. Physiological relevance in alcoholic patients", J. Biol. Chem.271(32):19058-65.
Landshultz, et al., 1996, "Regulation of scavenger receptor, class B, type I, a high density lipoprotein receptor, in liver and steroidogenic tissues of the rat", J. Clin. Invest. 98(4):984-995.
Larock, 1989, Comprehensive Organic Transformations; Ch. 6, VCH: New York, pp. 446-448.
Lazarow and Fujiki, 1985, "Biogenesis of peroxisomes", Annu Rev Cell Biol. 1:489-530.
Levin, et al., 1992, "9-cis retinoic acid stereoisomer binds and activates the nuclear receptor RXR alpha", Nature 355(6358):359-61.

(56) References Cited

OTHER PUBLICATIONS

Ludwig, et al., 1989, "Rapid and efficient synthesis of nucleoside 5'-0-(1-thiotriphosphates), 5'-triphosphates and 2',3'-Cyclophosphorothioates using 2-Chloro-4H-1,3,2-benzodioxaphosphorin-4-one", J. Org. Chem. 54:631-35.

Maddaford, et al., 1993, "A general asymmetric synthesis of (−)-alpha-Dimethylretrodendrin and its diastereomers", J. Org. Chem 58:4132-38.

March, J., 1992, Advanced Organic Chemistry: Reactions, Mechanisms, and Structure 4th ed., pp. 248-272, 1196-98, 437-438, 920-929.

Masamune, et al., "Tylonolide hemiacetal, the aglycone of tylosin, and its partial synthesis," J. Am. Chem. Soc. (1976) vol. 98, pp. 7874-7875.

Masayuma, et al., 2000, "Regio-and diastereocontrol in carbonyl allylation by 1-halobut-2-enes with Tin(II) halides", J Org Chem. 65(2):494-8.

McCune et al., "Effect of Mevinolin on Cholesterol Metabolism in Obese and Lean Zucker Rats," Biochemical Pharmacology (1987) vol. 36, pp. 875-879. (abstract only).

Menger, et al., 1981, "Synthetically useful oxidations at solid sodium permanganate surfaces", Tetrahedron Lett. 22:1655-56.

Miyashita, et al., 1977, "Pyridinium .rho.-Toluenesulfonate. A mild and efficient catalyst for the tetrahydropyranylation of alcohols", J. Org. Chem 42:3772-74.

Moffet, et al., 1963, "2-(1-Pyrrolidyl)Propanol", Org. Synth. Collect 4:834-5.

Mulzer, 1995, Comprehensive Organic Functional Group Transformations Oxford 5 pp. 161.

Myers, et al., 1992, "Studies on the thermal generation and reactivity of a class of (.alpha., .pi.)-1,4-biradicals", J. Am. Chem. Soc. 114:9369-86.

Nagano H., et al., "Stereoselectivitiy in the formation and radical reduction of cyclic bromoacetals, key intermediates for the synthesis of delta-hydroxy-and epilson-hydroxy-alpha-methylcarboxylic acid esters", Tetrahedron Letters, 2003, pp. 6867-6870, vol. 44, No. 36.

Nan F. et al. "Dual Function Glutamate-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.

Nemali, et al., 1988, "Comparison of constitutive and Inducible levels of expression of paroxisomal beta-oxidation and catalase genes in liver and extrahepatic tissues of rat", Cancer Res. 48(18):5316-24.

Nystrom, et al., 1947, "Reduction of Organic Compounds by Lithium Aluminum Hyride", J. Am. Chem. Soc. 69:1197-1199.

Nystrom, et al., 1949, "Lithium borohydride as a reducing agent", J. Am. Chem. 71:3245-47.

Ogata, et al., 1969, "Kinetics of the Baeyer-Villiger reaction of benzaldehydes with perbenzoic acid in aquoorganic solvents", J. Org. Chem. 34:3985-91.

Okamoto, et al., 1985, "Synthesis of Alkyl Dihydrogenphosphate by the Reaction of Alcohols and Silyl Polyphosphate", Bull Chem. Soc. Jpn. 58:3393-3394.

Olah, et al., 1979, "Transformations with Chlorotrimethylsilane/ Sodium Iodide, a Convenient In Situ Iodotrimethylsilane Reagent", J. Org. Chem 44:8, 1247-1251.

Olah, et al., 1984, "N-Formylmorpholine: A New and Effective Formylating Agent for the Preparation of Aldehydes and Dialkyl(1-Formylalkyl)phosphonates from Grignard or Organolithium Reagents", J. Org. Chem. 4.

Olah, et al., 1987, "Formylating Agents", Chem. Rev. 87:4, 671-686.

Oster, et al., 1983, "Generation and Reactions of the Dianion of 3-Hydroxy-5-methylisoxazole, a convenient β-keto Amide Synthon", J. Org. Chem 48:4307-4311.

Parra, et al., 1992, "A case-control study of lipoprotein particles in two populations at contrasting risk for coronary heart disease. The ECTIM Study", Arterioscler Thromb. 12:701-707.

PCT International Search Report and Written Opinion, PCT Application No. PCT/US2015/021677, dated Apr. 16, 2015, 8 pages.

Pop, et al., 1997, "Allylic and Phenolic Phosphate Esters of Dexanabinol", Org. Prep. And Proc. Int. 29:341-347.

Ramirez, et al. "Phosphorylation by means of cyclic enediol phosphates," Acc. Chem. Res. (1978) vol. 11, pp. 239.

Raunio, et al., 1957, "Addition of Propargyl Acetal to Cyclohexanone in the Presence of Sodamide", J. Org. Chem 22:570.

Reaven, 1993, "Role of Insulin resistance in human disease (syndrome X): an expanded definition", Annu Rev Med. 44:121-31.

Reddy and Lalwani, 1983, "Carcinogenesis by hepatic peroxisome proliferators: evaluation of the risk of hypolipidemic drugs and industrial plasticizers to humans", Crit Rev Toxicol. 12(1):1-58.

Rigotti, et al., 1996, "Regulation by adrenocorticotropic hormone of the in vivo expression of scavenger receptor class B type I (SR-BI), a high density lipoprotein receptor, in steroidogenic cells of the murine adrenal", J. Biol. Chem. 1996, vol. 271(52):33545-9.

Robins and Fasulo, 1997, "High density lipoproteins, but not other lipoproteins, provide a vehicle for sterol transport to bile", J Clin Invest. 98(3):380-4.

Rowe, "Handbook of Pharmaceutical Excipients, 6th Ed." 2009, Pharmaceutical press, pp. 129-133, 185-188, 317-324, 364-369, 404-407, 581-585, 651-653 and 663-666.

Sam, et al., 1972, "Crown Polyether Chemistry, Potassium Permanganate Oxidations in Benzene", J. Am. Chem. Soc. 94:4024.

Saulnier, et al., 1982, "Generation and Reactions of 3-Lithio-1-(phenylsulfonyl)Indole", J. Org. Chem 47:757.

Schaper, U.A. (1980) "Die gemischte Guerbet-Reaktion zwischen cyclischen und acyclischen Alkoholen," Fette, Seifen, Anstrichmittel, Industrieverlag von Hernhaussen kg, 82 (11): 454-456.

Shen, "Cover Up," Innovations in Pharm Tech 52, (2015), pp. 44-47.

Shirley, et al., 1995, "Metalation of pyrrole, 1-methylpyrrole, and 1-phenylpyrrole with n-Butyllithium", J. Org. Chem 20:225-31.

Sianesi, et al., 1971, "3.4-dihydro-1H-2.1-, 3.4-Dihydro-2H-1.2-und. 3.4-Dihydro-1H-2.3-benzothiazin-S.S-dioxid", Chem. Ber. 104:1880-91.

Silverman, The Organic Chemistry of Drug Design and Drug Interaction, 1992, pp. 15-22.

Skinner, et al., 1995, "Benzoylcyanamide from ethyl benzoylitioncarbomate", J. Am. Chem. Soc. 77:5440-42.

Smith, et al., 1957, "Nitrogen Compounds of the phosphoric and Phosphonic Acids, III, Preparation and Properties of Amides of Phenylphosphonic and Phenylphosphonothiolic Acids", J. Org. Chem. 22:265-267.

Song, et al., 1999, "Practical asymmetric synthesis of an endothelin receptor antagonist", J. Org. Chem. 64:9658-67.

Staels and Auwerx, 1998, "Regulation of apo A-I gene expression by fibrates", Atherosclerosis 137 Suppl:S19-23.

Stevens, et al., 1982, "Further studies on the utility of sodium hypochlorite in organic synthesis Selective oxidation of diols and direct conversion of aldehydes to esters," Tetrahedron Lett. 23:4647-4650.

Stowell, et al., 1995, "A new method for the phosphorylation of alcohols and phenols", Tetrahedron Lett. 36(11):1825-26.

Sundararaman, et al., 1978, "One step conversion of aldehydes to esters", Tetrahedron Lett. 19:1627-1628.

Sweeney, 1995, "Comprehensive Organic Functional Group Transformations", Oxford, vol. 2, pp. 104-109.

Taravel, et al., 1988, "Interglycosidic 13C-1H Coupling Constants", Tetrahedron Lett. 29:199-200.

Thompson et al., "Treatment with ETC-1002 along in in combination with ezetimibe lowers LDL cholesterol in hypercholesterolemic patients with or without statin intolerance," 2016, National Lipid Association, Journal of Clinical Lipidology, vol. 10, pp. 556-567.

Thums et al., "Epoxidation—a Consequence of Cell Damage," Chemical Monthly, 128 (4), 1997, pp. 411-420.

Kanai and Tomioka, "Catalytic Asymmetric Conjugate Addition of Grignard Reagents Mediated by Copper (I)-Chiral Bidentate Phosphine Complex", Tetrahedron Lett. 36:4275-4278; 1995.

(56) References Cited

OTHER PUBLICATIONS

Tontonoz, et al., 1994, "Adipocyte-specific transcription factor ARF6 is a heterodimeric complex of two nuclear hormone receptors, PPAR gamma and RXR alpha", Nucleic Acids Res. 22(5):5628-34.
Uhlmann, et al., 1986, "Chemical 5'-phosphorylation of oligonucleotides valuable in automated DNA synthesis", Tetrahedron Lett. 27:1023-26.
Ulrich, et al., 1995, "Cultured hepatocytes as investigational models for hepatic toxicity: practical applications in drug discovery and development", Toxicol Lett. 82/83:107-15.
Urata, et al., 1991, "Transition metal complex catalyzed carbonylation of organic halides in the presence of molecular sieves instead of base," Tetrahedron Lett. 32:36, 4733-36.
Vamecq and Draye, 1989, "Pathophysiology of peroxisomal .beta.-oxidation", Essays Biochem. 24: 115-225.
Vippagunta, S. et al., "Crystalline Solids," Advanced Drug Delivery Reviews (2001) vol. 48, pp. 2-26. (abstract only).
Vogtle, et al., 1987, "Doubly Clamped Cope Systems", J. Org. Chem. 52:5560-5564.
Williams, et al., 1988, "Bromine as an oxidant for direct conversion of aldehydes to esters", Tetrahedron Lett. 29:5087-90.
Wilson, et al., 1982, "A novel, nonoxidative method for the conversion of aldehydes to esters", J. Org. Chem. 47:1360-61.
Wroblewski and Ladue, 1995, "Lactic dehydrogenase activity in blood", Proc. Soc. Exp. Biol. Med. 90:210-213.
Xu, et al., 1989, "The retinoblastoma susceptibility gene product: a characteristic pattern in normal cells and abnormal expression in malignant cells", Onocogene 4: 807-812.
Yamamoto, "Asymmetric synthesis of 5-and 6-membered lactones from cyclic substrates bearing a C2-chiral auxiliary", J. Org. Chem., 1991, pp. 1112-1119, vol. 35, No. 21.
Yanagisawa, et al., 1994, "Allylbarium Reagents: Unprecedented regio- and stereoselective allylation reactions of carbonyl compounds", J. Am. Chem. Soc. 116:6130-6141.
Yoshikawa, et al., 1983, "Catalytic Regioselective Dehydrogenation of Unsymmetrical alpha Omega-Diols Using Ruthenium Complexes", Tetrahedron Lett. 26:2677-2680.
Yu, et al., 1988, "A novel reagent for the synthesis of myo-inositol phosphates: N,N-diisopropyl dibenzyl phosphoramidite", Tetrahedron Lett. 29:979-82.
Yunker, et al., 1978, "Alpha-oxygenated fatty acids occurring as amides of 2-methylene beta-alanine in a marine sponge", Tetrahedron Lett. 47:4651-52.
U.S. Appl. No. 15/859,279, filed Dec. 29, 2019, Fixed Dose Formulations, Abdelnasser et al.

* cited by examiner

FIXED DOSE COMBINATIONS AND FORMULATIONS COMPRISING ETC1002 AND EZETIMIBE AND METHODS OF TREATING OR REDUCING THE RISK OF CARDIOVASCULAR DISEASE

BACKGROUND

Field of the Invention

This application relates to methods and compositions useful for treating cardiovascular conditions or reducing the risk of cardiovascular conditions. Statins are the cornerstone of prevention and treatment of cardiovascular disease, but can produce statin-associated muscle symptoms in 5% to 29% of patients. Muscle symptoms including pain, stiffness, cramping, or weakness, usually without serum creatine kinase (CK) elevations, are the primary manifestation of statin intolerance. This application relates to methods and compositions comprising fixed doses of ETC-1002 and Ezetimibe for the treating or reducing the risk of cardiovascular disease.

Low-density lipoprotein cholesterol (LDL-C) is a well-established risk factor for cardiovascular disease. However, many patients, for example those with hypercholesterolemia, fail to reduce LDL-C to desired levels with traditional therapies. Existing residual cardiovascular risk, especially observed in high-cholesterol patients, and despite the advances of new cholesterol-reducing drugs, has encouraged a search for new, non-traditional pharmaceuticals. New pharmaceutical drugs have been developed and are effective at reducing cholesterol levels in the human body. Unfortunately, these drugs also induce negative side-effects. Many of the compounds which have shown to be potent for inhibiting the enzymes of cholesterol biosynthesis are also systemically toxic. Thus, there is a need for new pharmaceutical formulations which are both effective and safe for reducing cholesterol.

SUMMARY

This application relates to methods and compositions comprising fixed doses of ETC-1002 and Ezetimibe for the treating or reducing the risk of cardiovascular disease.

ETC-1002 is an agent that lowers low-density lipoprotein cholesterol (LDL-C) by direct inhibition of hepatic adenosine triphosphate citrate lyase, leading to reduced de novo cholesterol synthesis and increased LDL receptor expression. ETC-1002 administered in doses from 120 mg to 240 mg daily reduced LDL-C by 27% to 43% in phase 2a clinical trials of various hypercholesterolemic populations including patients with type 2 diabetes mellitus and patients with muscle-related statin intolerance. The present application discloses on a method using fixed dose combination of ETC-1002 and Ezetimibe based on results from studies, disclosed herein, that compared the efficacy and safety of ETC-1002 monotherapy (120 mg or 180 mg daily) and ETC-1002 combined with Ezetimibe 10 mg (EZE) versus EZE monotherapy among hypercholesterolemic patients with or without a history of statin-related muscle symptoms.

Ezetimibe is a compound which lowers cholesterol levels in the body by decreasing cholesterol absorption in the small intestine. It can be used alone or in combination with statin therapy. Although effective for lowering the overall cholesterol count in a patient, clinical results have never shown Ezetimibe could have a statistically significant impact on major cardiovascular event outcomes, for example those associated with a heart attack or stroke. Moreover, Ezetimibe has not been shown effective for reducing atherosclerosis.

The inventors have found that both Ezetimibe and ETC-1002 directly affect a lower LDL-C level (within 2 weeks) in patients which are statin-tolerant and in patients which are statin-intolerant. Additionally, the inventors find that combining these two therapies leads to cooperative activity, even lower LDL-C levels, and a favorable clinical treatment. Accordingly, the present invention is directed toward cholesterol-lowering compositions comprising Ezetimibe and ETC-1002. These compositions lead to further reductions in total cholesterol, and specifically LDL-C, in patients.

The present application also discloses a method of lowering cholesterol using fixed dose combination of ETC-1002 and Ezetimibe. Based on observations in on-going studies, combination therapy with ETC-1002 and a fixed dosage of Ezetimibe has comparable efficacy and safety to that of ETC-1002 alone, or combined with a fixed, low to medium dosage of one or more statins. Of course, combination therapy with a fixed dosage ETC-1002 and Ezetimibe is also significantly greater versus statin or ETC-1002 monotherapy (120 mg or 180 mg daily) in patients with or without a history of statin-related muscle symptoms. The combination therapy shows a significantly greater efficacy and safety profile even in acute hypercholesterolemic patients.

In one aspect, methods and compositions of present invention even lower cholesterol (LDL-C, and other markers for example: triglycerides, ApoB, hsCRP, non-HDL-C, HDL-C, LDL particle number, ApoA1, and lower the risk of cardiovascular disease and any AEs) in patients with persistently elevated LDL-C, despite stable statin therapy at high of a dosages from 10 mg to 80 mg of statins.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Advantages and Utility

Figure 1:
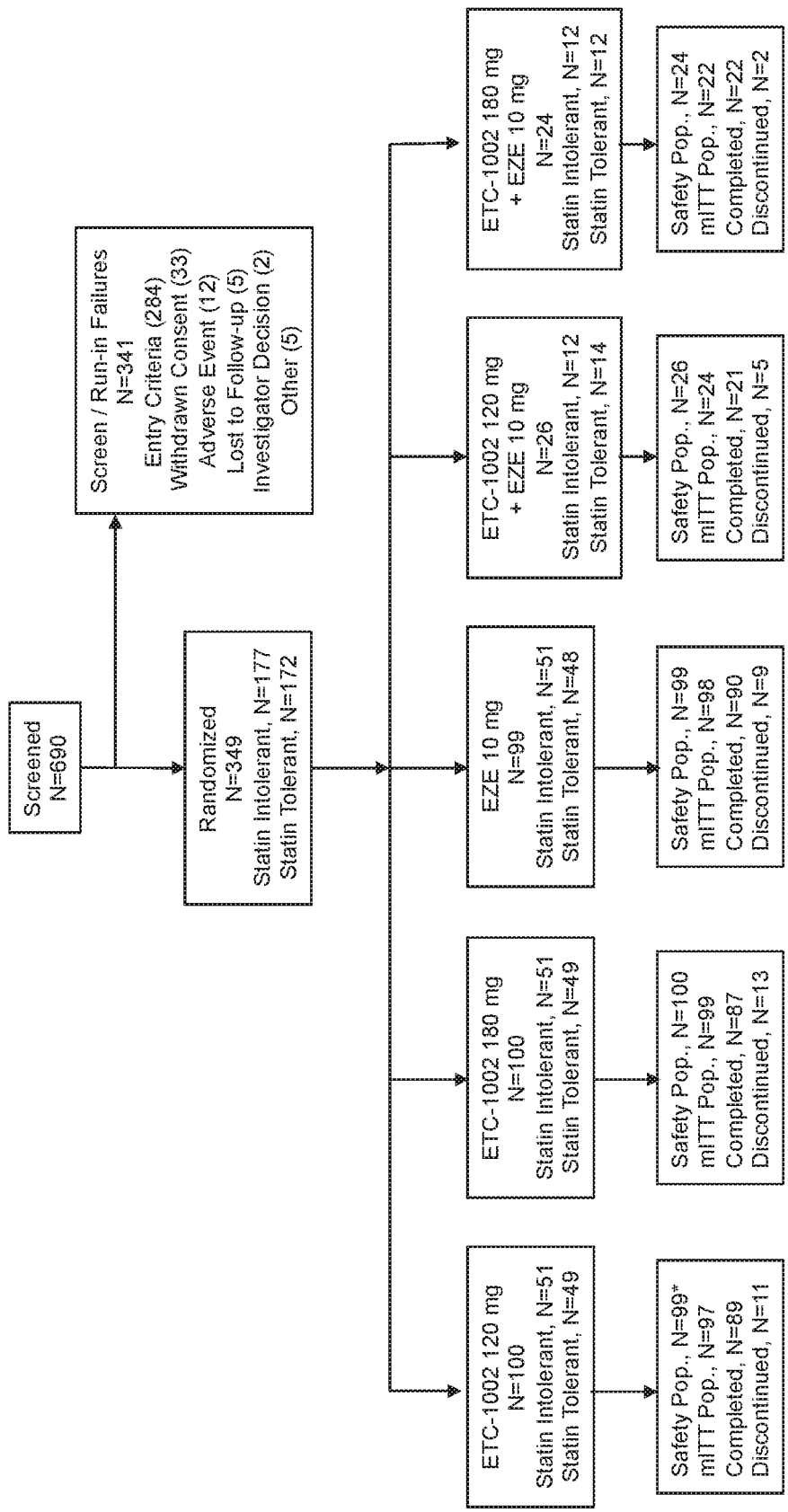
FIG. 1: Disposition of Patients. *One patient who was statin tolerant was randomized but discontinued before receiving study drug. EZE=Ezetimibe; mITT=modified intent-to-treat; Pop.=population.

Briefly, and as described in more detail below, described herein are compositions, methods of making the said compositions and methods for treating cardiovascular disease or reducing the risk of cardiovascular disease using fixed-dose combinations of Ezetimibe and ETC-1002. The advantages for this approach are numerous and include, but are not limited to, increased reduction of cholesterol and low density lipoprotein levels in patients treated with the fixed-dose combinations of Ezetimibe and ETC-1002 than when patients are treated with either Ezetimibe or ETC-1002 alone. As described above, Statins are the cornerstone of prevention and treatment of cardiovascular disease, but can produce statin-associated muscle symptoms in 5% to 29% of patients. Statin-associated muscle symptoms are an important clinical problem because statin discontinuation in hypercholesterolemic patients increases cardiovascular risk. Patients who discontinue statin treatment because of intolerance show a trend toward decreased 8-year survival compared with patients who continue statin therapy. Hence, there is a significant need for cardiovascular therapies for patients that exhibit muscle-related statin intolerance Definitions Terms used in the claims and specification are defined as set forth below unless otherwise specified.

Terms used in the claims and specification are defined as set forth below unless otherwise specified. Further, if any term or symbol used herein is not defined as set forth below, it shall have its ordinary meaning in the art.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

The term "ameliorating" refers to any therapeutically beneficial result in the treatment of a disease state, e.g., an inflammatory disease state, including lessening in the severity or progression, remission, or cure thereof. In some embodiments, "ameliorating" includes prophylaxis of a disease state.

The term "in vitro" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can, in some embodiments, be a "prophylactically effective amount" as prophylaxis can be considered therapy.

The compounds of the present technology can exist as solvates, especially hydrates. Hydrates may form during manufacture of the compounds or compositions comprising the compounds, or hydrates may form over time due to the hygroscopic nature of the compounds. Compounds of the present technology can exist as organic solvates as well, including DMF, ether, and alcohol solvates among others. The identification and preparation of any particular solvate is within the skill of the ordinary artisan of synthetic organic or medicinal chemistry.

"Subject" refers to a mammalian organism treated using a compound of the present invention. The "subject" can be a human or non-human mammalian organism.

"Tautomer" refer to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Treating" or "treatment" of a disease or disorder in a subject refers to 1) preventing the disease or disorder from occurring in a subject that is predisposed or does not yet display symptoms of the disease or disorder; 2) inhibiting the disease or disorder or arresting its development; or 3) ameliorating or alleviating the cause of the regression of the disease or disorder.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

Unless defined otherwise, all technical and scientific terms used herein have the meaning commonly understood by a person skilled in the art to which this invention belongs.

Herein any and all heteroaryl and heterocycloalkyl substituents may contain up to four heteroatoms selected from the group consisting of: O, N, and S.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be Substituted one more time (at from one to three positions).

It is understood that the above definitions are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Abbreviations

AE is an abbreviation for adverse event
CK in an abbreviation for creatine kinase
EZE=is an abbreviation for Ezetimibe
HDL-C is an abbreviation for high-density lipoprotein cholesterol
CRP=is an abbreviation for high-sensitivity C-reactive protein
LDL-C is an abbreviation for low-density lipoprotein cholesterol
LS is an abbreviation for least-squares
NCEP ATP-III is an abbreviation for National Cholesterol Education Program Adult Treatment Panel III
non-HDL-C is an abbreviation for non-high-density lipoprotein cholesterol
VLDL is an abbreviation for very-low-density lipoprotein Therapy Disclosed herein is a method comprising administrating a fixed-dose combination of a fixed dose of ETC-1002 or an analog thereof and a fixed dose of Ezetimibe or an analog thereof to a subject in need thereof, optionally wherein ETC-1002 is administered at a fixed dose of 120 mg or at a fixed dose of 180 mg and Ezetimibe is administered at a fixed dose of 10 mg.

In some aspects, the method decreases the level of low density lipoprotein cholesterol (LDL-C) in the subject below that of a control subject receiving a placebo, a fixed 120 mg dose of ETC-1002, a fixed 180 mg dose of ETC-1002, or a fixed 10 mg dose of Ezetimibe, and optionally wherein the method treats or reduces the risk of cardiovascular disease in the subject.

In some aspects, ETC-1002 is administered at a fixed dose of 120 mg or at a fixed dose of 180 mg and Ezetimibe is administered at a fixed dose of 10 mg.

In some aspects, the subject has hypercholesterolemia, and wherein the method further comprises treating hypercholesterolemia.

In some aspects, the method treats or reduces the risk of cardiovascular disease in the subject.

In some aspects, the method decreases the level of cholesterol in the subject below that of a control subject receiving a placebo, a fixed 120 mg dose of ETC-1002, a fixed 180 mg dose of ETC-1002, or a fixed 10 mg dose of Ezetimibe.

In some aspects, the method decreases the level of LDL-C in the subject below that of a control subject receiving a placebo, a fixed 120 mg dose of ETC-1002, a fixed 180 mg dose of ETC-1002, or a fixed 10 mg dose of Ezetimibe. In some aspects, the method decreases the level of C-reactive protein (hsCRP) in the subject below that of a control subject receiving a placebo, a fixed 120 mg dose of ETC-1002, a fixed 180 mg dose of ETC-1002, or a fixed 10 mg dose of Ezetimibe. In some aspects, the method decreases the level of apolipoprotein B (ApoB) in the subject below that of a control subject receiving a placebo, a fixed 120 mg dose of ETC-1002, a fixed 180 mg dose of ETC-1002, or a fixed 10 mg dose of Ezetimibe. In some aspects, the method decreases the level of non-high density lipoprotein-cholesterol in the subject below that of a control subject receiving a placebo, a fixed 120 mg dose of ETC-1002, a fixed 180 mg dose of ETC-1002, or a fixed 10 mg dose of Ezetimibe. In some aspects, the method decreases the level of triglycerides in the subject below that of a control subject receiving a placebo, a fixed 120 mg dose of ETC-1002, a fixed 180 mg dose of ETC-1002, or a fixed 10 mg dose of Ezetimibe. In some aspects, the method decreases the LDL particle number in the subject below that of a control subject receiving a placebo, a fixed 120 mg dose of ETC-1002, a fixed 180 mg dose of ETC-1002, or a fixed 10 mg dose of Ezetimibe.

In some aspects, LDL-C is decreased in the subject by at least 30, 35, 40, 43, 45, 48, or 50% relative to baseline. In some aspects, non HDL-C is decreased in the subject by at least 30, 35, 37, 40, 42, or 45% relative to baseline. In some aspects, hsCRP is decreased in the subject by at least 20, 25, 26, 30, 35, 38, or 40% relative to baseline.

In some aspects, Ezetimibe and ETC-1002 are each administered orally. In some aspects, Ezetimibe and ETC-1002 are each administered at least once daily. In some aspects, Ezetimibe and ETC-1002 are each administered at least once daily for at least 1, 2, 3, 4, 5, 6, 7, 8, 9, 10, 11, or 12 week(s).

In some aspects, the subject has dyslipidemia. In some aspects, the subject has hypercholesterolemia. In some aspects, the subject is obese, optionally wherein the BMI of the subject is 18-45 kg/m$^2$. In some aspects, the subject is statin tolerant. In some aspects, the subject is statin intolerant. In some aspects, the subject is unable to tolerate at least two statins including one statin at the lowest FDA approved dose due to muscle-related symptoms such as pain, aches, weakness, or cramping that began or increased during statin therapy and resolved when statin therapy was discontinued.

In some aspects, the subject has a baseline LDL-C level of 130-220 mg/dL. In some aspects, the subject has a baseline triglycerides level of less than or equal to 400 mg/dL.

In some aspects, Ezetimibe and ETC-1002 are administered simultaneously. In some aspects, Ezetimibe and ETC-1002 are administered separately.

Also disclosed herein is a method of treating cardiovascular disease or reducing the risk of cardiovascular disease in a subject, comprising administrating a fixed-dose combination of a fixed dose of ETC-1002 or an analog thereof and a fixed dose of Ezetimibe or an analog thereof to a subject in need thereof, optionally wherein ETC-1002 is administered at a fixed dose of 120 mg or at a fixed dose of 180 mg and Ezetimibe is administered at a fixed dose of 10 mg, optionally wherein the method decreases the level of low density lipoprotein cholesterol (LDL-C) in the subject below that of a control subject receiving a placebo, a fixed 120 mg dose of ETC-1002, a fixed 180 mg dose of ETC-1002, or a fixed 10 mg dose of Ezetimibe, and optionally wherein the subject has hypercholesterolemia.

Also disclosed herein is a pharmaceutical composition comprising ETC-1002 and Ezetimibe, optionally wherein ETC-1002 is present at a fixed dose of 120 mg or 180 mg and Ezetimibe is present at a fixed dose of 10 mg.

In some aspects, the composition further comprises a pharmaceutically acceptable vehicle. In some aspects, ETC-1002 is present at a fixed dose of 120 mg or 180 mg and Ezetimibe is present at a fixed dose of 10 mg. In some aspects, the composition is formulated for oral delivery. In some aspects, the composition is formulated for administration once daily.

In some aspects, the method decreases the level of apolipoprotein B (ApoB) in the subject below that of a control subject receiving a placebo, a fixed 120 mg dose of ETC-1002, a fixed 180 mg dose of ETC-1002, or a fixed 10 mg dose of Ezetimibe.

In some aspects, the method decreases the level of apolipoprotein A1 (ApoA1) in the subject below that of a control subject receiving a placebo, a fixed 120 mg dose of ETC-1002, a fixed 180 mg dose of ETC-1002, or a fixed 10 mg dose of Ezetimibe.

In some aspects, the method increases the level of ApoA1 in the subject above that of a control subject receiving a placebo, a fixed 120 mg dose of ETC-1002, a fixed 180 mg dose of ETC-1002, or a fixed 10 mg dose of Ezetimibe.

In some aspects, the method does not change the level of ApoA1 in the subject compared to that of a control subject receiving a placebo, a fixed 120 mg dose of ETC-1002, a fixed 180 mg dose of ETC-1002, or a fixed 10 mg dose of Ezetimibe.

In some aspects, the method decreases the ratio of ApoB to ApoA1 in the subject above that of a control subject receiving a placebo, a fixed 120 mg dose of ETC-1002, a fixed 180 mg dose of ETC-1002, or a fixed 10 mg dose of Ezetimibe.

In some aspects, the method decreases the number of very low lipoprotein particles (VLDL) in the subject below that of a control subject receiving a placebo, a fixed 120 mg dose of ETC-1002, a fixed 180 mg dose of ETC-1002, or a fixed 10 mg dose of Ezetimibe.

In some aspects, the method decreases the size of very low lipoprotein particles (VLDL) in the subject below that of a control subject receiving a placebo, a fixed 120 mg dose of ETC-1002, a fixed 180 mg dose of ETC-1002, or a fixed 10 mg dose of Ezetimibe.

Compounds

Combinations of Ezetimibe and ETC-1002 are described herein.

Formula I below shows ETC-1002 and analogs of ETC-1002.

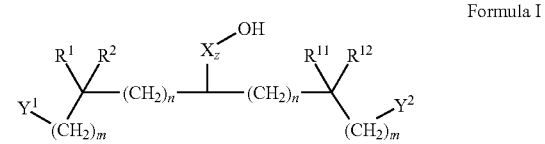

Formula I wherein each occurrence of m is independently an integer ranging from 0 to 5; (b) each occurrence of n is independently an integer ranging from 3 to 7; (c) X is $(CH_2)$, or Ph, wherein z is an integer from 0 to 4 and Ph is a 1,2-, 1,3-, or 1,4 substituted phenyl group; (d) each occurrence of $R^1$, $R^2$, $R^{11}$, and $R^{12}$ is independently H, $(C_1-C_6)$alkyl, $(C_2-C_6)$alkenyl, $(C_2-C_6)$alkynyl, phenyl, or benzyl, wherein $R^1$, $R^2$, $R^{11}$, and $R^{12}$ are not each simultaneously H; and (e) each occurrence of $Y^1$ and $Y^2$ is independently $(C_1-C_6)$alkyl, OH, COOH, $COOR^3$, $SO_3H$,

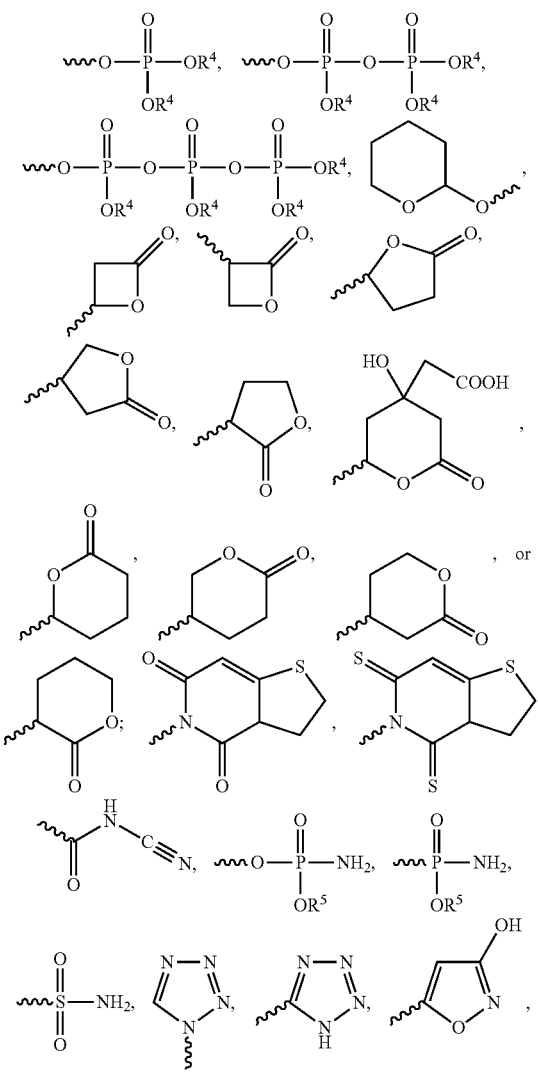

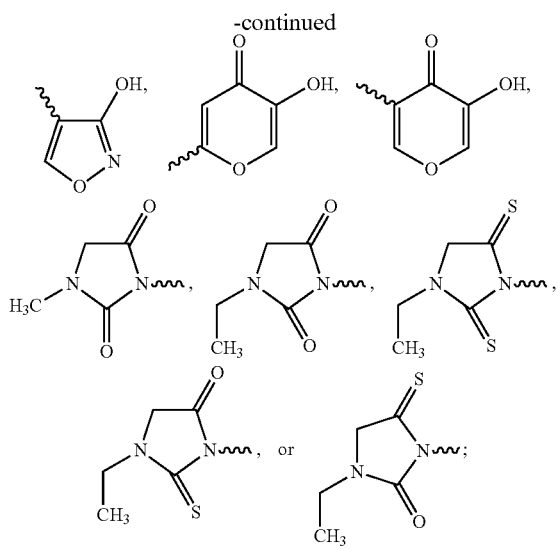

wherein: (i) $Y^1$ and $Y^2$ are not each simultaneously ($C_1$-$C_6$)alkyl; (ii) $R^3$ is ($C_1$-$C_6$)alkyl, ($C_2$-$C_6$)alkenyl, ($C_2$-$C_6$)alkynyl, phenyl, or benzyl and is unsubstituted or substituted with one or more halo, OH, ($C_1$-$C_6$)alkoxy, or phenyl groups, (iii) each occurrence of $R^4$ is independently H, ($C_1$-$C_6$)alkyl, ($C_2$-$C_6$)alkenyl, or ($C_2$-$C_6$)alkynyl and is unsubstituted or substituted with one or two halo, OH, $C_1$-$C_6$, alkoxy, or phenyl groups; and (iv) each occurrence of $R^5$ is independently H, ($C_1$-$C_6$) alkyl, ($C_2$-$C_6$)alkenyl, or ($C_2$-$C_6$)alkynyl.

Structure of ETC-1002:

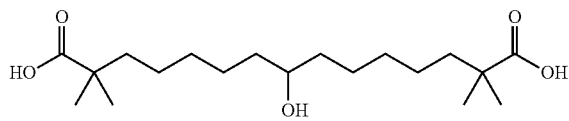 [SMILES: CC(C)(CCCCCC(O)CCCCCC(C)(C)C(=O)O)C(=O)O]

ETC-1002 can be referred to as 8-hydroxy-2,2,14,14 tetramethylpentadecanedioic acid.

Formula (II) below shows Ezetimibe and analogs of Ezetimibe:

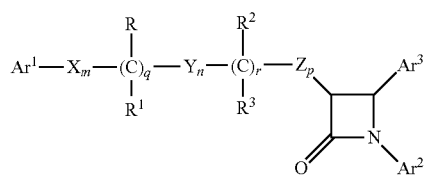

(II)

wherein in Formula (II) above or a salt thereof, wherein: $Ar^1$ and $Ar^2$ are independently selected from the group consisting of aryl and $R^4$-substituted aryl; $Ar^3$ is aryl or $R^5$-substituted aryl; X, Y and Z are independently selected from the group consisting of —$CH_2$—, —CH(lower alkyl)- and —C(dilower alkyl)-; R and $R^2$ are independently selected from the group consisting of —$OR^6$, —$O(CO)R^6$, —$O(CO)OR^9$ and —$O(CO)NR^6R^7$; $R^1$ and $R^3$ are independently selected from the group consisting of hydrogen, lower alkyl and aryl; q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5; $R^4$ is 1-5 substituents independently selected from the group consisting of lower alkyl, —$OR^6$, —$O(CO)R^6$, —$O(CO)OR^9$, —$O(CH_2)_{1-5}$ $OR^6$, —$O(CO)NR^6R^7$, —$NR^6R^7$, —$NR^6(CO)R^7$, —$NR^6$ $(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, -(lower alkylene)$COOR^6$, —CH=CH—$COOR^6$, —$CF_3$, —CN, —$NO_2$ and halogen; $R^5$ is 1-5 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)$ $NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}$ $CONR^6R^7$, -(lower alkylene)$COOR^6$ and —CH=CH—$COOR^6$; $R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Ezetimibe can be referred to as 1-(4-fluorophenyl)-3(R)-[3(S)-(4-fluorophenyl)-3-hydroxypropyl)]-4(S)-[4-(phenyl-methoxy)phenyl]-2-azetidinone; or (3R,4S)-1-(4-fluorophenyl)-3-[(3S)-3-(4-fluorophenyl)-3-hydroxypropyl]-4-(4-hydroxyphenyl)azetidin-2-one.

The structure of Ezetimibe is:

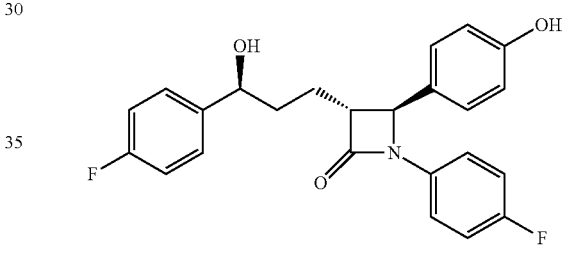

It is acknowledged that any and all analogs of ETC-1002 according to Formula I can be used in any of the methods and/or compositions or formulations disclosed herein. It is further acknowledged that any and all analogs of ETC-1002 according to Formula II can be used in any of the methods and/or compositions or formulations disclosed herein.

Synthesis of ETC-1002 and Ezetimibe

ETC-1002 and the process of synthesis of ETC-1002 is disclosed in the issued U.S. Pat. No. 7,335,799. The details of this process can be found in the published U.S. patent publication No. US2005-0043278 A1, in paragraphs [0247]-[0343] of the specification, each of which is herein incorporated by reference.

Ezetimibe and the process of synthesis of Ezetimibe is disclosed in the issued U.S. Pat. No. 5,631,365. The details of this process can be found in the specification, beginning on page 4 right column, line 43 through page 11 right column, line 65, each of which is herein incorporated by reference.

Any other synthetic modifications for any analogs of these two organic compounds, which may include for example unique or alternative aromatic substituent groups for the Ezetimibe, are within the purview of the skilled artisan. For example, the skilled artisan will be able to use synthetic reference texts to incorporate unique or desired substituted-aryl or even heteroaryl ring systems into a final Ezetimibe analog compound. Such references include, but are not limited to: as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989), T. W. Greene and P.G.M. Wuts, *Protecting Groups in Organic Synthesis*, Third Edition, Wiley, New York, 1999.

Methods of Use

The present invention provides methods for the treatment or prevention of a cardiovascular disease, comprising administering to a subject fixed doses of compounds or a composition comprising compounds of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction; cerebral infarction and restenosis.

The present invention provides methods for the treatment or prevention of a dyslipidemia comprising administering to a subject fixed doses of compounds or a composition comprising compounds of the invention and a pharmaceutically acceptable vehicle. As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol-/about_level.html and http://www.nhlbi.nih.gov/health/public/heart/chol/hb-c_what.html, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. .beta.-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

Pharmaceutical Compositions

Methods for treatment of cardiovascular diseases are also encompassed by the present invention. Said methods of the invention include administering a therapeutically effective amount of Ezetimibe and ETC-1002. The fixed dose combination of Ezetimibe and ETC-1002 can be formulated in pharmaceutical compositions. These compositions can comprise, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, pill, powder or liquid form. A tablet or pill can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In one aspect, pharmaceutical compositions of the present invention are created from one or more of the compounds disclosed herein and are in the form of a pill.

In another aspect, herein provided is a method for lowering cholesterol or the associated markers disclosed herein (HDL-C, ApoA1, etc.) or for the treatment or prevention of a cardiovascular disease or dyslipoproteinemias and/or dyslipidemias, comprising administering to a subject a pharmaceutical composition in the form of a pill comprising ETC-1002 at a fixed dose of 120 mg or 180 mg and Ezetimibe at a fixed dose of 10 mg.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a small molecule or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

It must be noted that, as used in the specification and the appended claims, the singular forms "a," "an" and "the" include plural referents unless the context clearly dictates otherwise.

Methods

Brief Description of Clinical Study and Results.

A phase 2b, multicenter, double-blind trial evaluated 348 hypercholesterolemic patients (LDL-C, 130 to 220 mg/dL) with (n=177) or without (n=171) muscle-related intolerance to ≥2 statins; 1 at lowest approved dose. Subjects were randomized to 12 weeks of treatment with ETC-1002 120 mg or ETC-1002 180 mg (both alone), EZE alone, ETC-1002 120 mg plus EZE, or ETC-1002 180 mg plus EZE. The percent change in LDL-C at week 12 in each of the 4 ETC-1002 treatment groups was compared with that in the EZE monotherapy group.

Of 690 patients screened, 341 were excluded, mainly for failure to satisfy inclusion criteria (FIG. 1). Of the 349 randomized patients (177 statin intolerant and 172 statin tolerant), 309 patients completed the study. The 40 who discontinued participation did so most commonly because of AEs. A higher percentage of statin-tolerant patients (93%) than statin-intolerant patients (84%) completed the study. The safety population included 348 patients as 1 statin-tolerant patient discontinued before receiving any study drug.

Most patients were non-Hispanic Caucasians with similar numbers of men and women (Table 1). Mean age, baseline lipid values, and National Cholesterol Education Program Adult Treatment Panel (NCEP ATP) III risk category were slightly higher in statin-intolerant patients. The most common prestudy statin-associated muscle complaints were bilateral calf and thigh pain (data not shown). Most statin-intolerant patients historically experienced the onset of statin-associated muscle symptoms within 1 to 2 weeks of statin initiation and most had resolution of symptoms within 1 to 2 weeks of discontinuation.

Study Objectives.

The primary objective was to assess the LDL-C—lowering effect of ETC-1002 monotherapy (120 mg or 180 mg daily) versus EZE monotherapy in hypercholesterolemic patients with or without statin intolerance. Secondary objectives were to characterize the dose response of ETC-1002, evaluate the impact of treatment on other lipid and cardiometabolic biomarkers, compare the LDL-C—lowering effect of ETC-1002 plus EZE combination therapy with EZE monotherapy, and characterize the safety and tolerability of the treatment regimens, including muscle-related adverse events (AEs).

Study Population.

Medically stable, hypercholesterolemic men and women aged 18 through 80 years with a body mass index between 18 to 45 kg/m² were included in the study. Eligible patients had fasting, calculated LDL-C values between 130 and 220 mg/dL and a fasting triglyceride level ≤400 mg/dL after washout of lipid-regulating drugs. The study population included both statin-tolerant and statin-intolerant participants. Statin intolerance was defined as the inability to tolerate ≥2 statins because of muscle-related symptoms such as pain, weakness, or cramping that began or increased during statin therapy and resolved on statin discontinuation. At least 1 statin must have been administered at the lowest approved daily dose, defined as rosuvastatin 5 mg, atorvastatin 10 mg, simvastatin 10 mg, lovastatin 20 mg, pravastatin 40 mg, fluvastatin 40 mg, or pitavastatin 2 mg. Treatment with less than the lowest approved daily dose of a statin (i.e., skipping days) was considered equivalent to not tolerating 1 statin at the lowest approved daily dose. Patients were excluded if they had clinically significant cardiovascular disease; type 1 diabetes mellitus; uncontrolled type 2 diabetes mellitus; non-statin related musculoskeletal complaints; uncorrected hypothyroidism; liver or renal dysfunction; unexplained CK elevations off statin treatment >3 times the upper limit of normal; ingested <80% of drug during single-blind run-in; or used anticoagulants, systemic corticosteroids, cyclosporine, metformin, or thiazolidinediones within 3 months of screening.

Overall Study Design and Plan.

This phase 2b, randomized, double-blind, active comparator-controlled, parallel-group study was conducted at 70 sites in the United States from Sep. 16, 2013 to Aug. 7, 2014 and consisted of a 6-week screening phase (week −6 to week 0) and a 12-week double-blind treatment period (week 0 to week 12). Patients underwent a 5-week washout of all lipid-regulating drugs and dietary supplements and abstained from these drugs and supplements throughout the study. Patients also underwent a 5-week patient-only-blinded placebo run-in during the screening period (week −5 to week 0). This single-blind placebo run-in period was used to eliminate patients with muscle-related AEs during placebo treatment. Patients reporting new or worsening, unexplained muscle-related AEs during this run-in period were excluded from the study.

Patients were stratified (1:1) by history of statin intolerance and randomized at week 0 in a 4:4:4:1:1 ratio to once-daily treatment with capsules containing ETC-1002 120 mg, ETC-1002 180 mg, EZE, ETC-1002 120 mg plus EZE, or ETC-1002 180 mg plus EZE. Patients were seen at weeks −6, −5, −3, −1, 0, 2, 4, 8, and 12. A contract laboratory (Medpace Inc., Cincinnati, Ohio), performed all clinical laboratory tests. LDL-C was calculated using the Friedewald equation. Phlebotomy was performed after a minimum 12-hour fast (water was allowed) and only if the patient took their dose of study drug the previous day.

Individual institutional review boards approved the clinical study protocol and informed consent documents. Written informed consent was obtained from all participants before any study-related procedures.

Efficacy Endpoints.

The primary endpoint was the percent change from baseline to week 12 in calculated LDL-C in patients treated with ETC-1002 monotherapy versus those treated with EZE alone. Secondary endpoints included the dose-response relationship between ETC-1002 and the percent change in LDL-C from baseline to week 12, the percent change in LDL-C from baseline to week 12 in patients treated with ETC-1002 plus EZE versus those treated with EZE alone, and the percent change from baseline to week 12 for all treatment groups in LDL particle number, apolipoprotein B, total cholesterol, non-high-density lipoprotein cholesterol (non-HDL-C), HDL-C, HDL particle number, apolipoprotein A-I, triglycerides, very-low-density lipoprotein (VLDL) particle number, and high-sensitivity C-reactive protein (CRP). Lipoprotein particle number was measured using nuclear magnetic resonance imaging.

Safety Endpoints.

The safety of ETC-1002 was assessed using treatment-emergent AEs; hematology, serum chemistry, and urinalysis laboratory values; physical examination findings; vital sign measurements; electrocardiogram (ECG) readings; weight; and ankle and waist circumference measurements. AEs were coded using the *Medical Dictionary for Regulatory Activities* version 16.0 and evaluated by the investigator for severity and relation to study drug. Muscle-related AEs were defined as those from the system organ class of musculoskeletal and connective tissue disorders, except for those that were not obviously muscle related. Terms included in the muscle-related AE analysis were selected from this system organ class after database lock and before unblinding.

Statistical Plan and Analyses.

The study was designed to include 322 patients: 92 patients in each monotherapy group and 23 patients in each combination therapy group. Sample size calculations were performed using nQuery Advisor® version 7.0 (Statistical Solutions, Cork, Ireland). The sample size of 92 patients per monotherapy group was expected to provide 90% power to detect a difference of 10% in the absolute percent change from baseline to week 12 in LDL-C between either ETC-1002 treatment group and the EZE monotherapy group. This calculation was based on a 2-sided t test at the 5% level of significance and assumed a common standard deviation of 15% in the statin-tolerant patients and 22% in the statin-intolerant patients with a dropout rate of 15%.

Efficacy analyses were performed on the modified intent-to-treat population, which consisted of randomized patients who had a baseline assessment, received at least 1 dose of study medication, and had at least 1 on-treatment assessment, excluding assessments taken more than 2 days after a dose of study drug. Safety analyses were performed on the safety population, which included randomized patients who received at least 1 dose of study drug. Baseline patient characteristics were summarized for the safety population by treatment group and statin-tolerance subgroup.

An analysis of covariance was used to compare each ETC-1002 treatment group with EZE monotherapy for each of the efficacy endpoints. The primary model included the effects of treatment and statin intolerance and the baseline value as a covariate. Baseline was defined as the mean of values from weeks −1 and 0 for LDL-C, non-HDL-C, total cholesterol, HDL-C, and triglycerides. For all other lipid and biomarker measures, baseline was defined as the last value before the first dose of study drug. Missing values at week 12 were imputed using the last-observation-carried-forward procedure. When LDL-C could not be calculated (i.e., triglycerides >400 mg/dL), beta-quantification measurements were used to determine LDL-C values. Least-squares (LS) means and standard errors were obtained for each treatment group; differences in LS means and p-values were obtained for the treatment comparisons. Graphical methods (e.g., normal probability plot and histogram of residuals, plot of residuals vs. predicted values) or analytical methods (e.g., Shapiro-Wilk test), or both, were used to assess the model assumptions. Because of departures from normality observed in the parameters of triglycerides, CRP, and VLDL particle number, nonparametric analyses were performed for these measures, with p-values obtained from the Wilcoxon rank-sum test and median values presented.

Actual values, changes from baseline, and percent changes from baseline in calculated LDL-C and secondary lipid and biomarker measures were summarized using descriptive statistics by treatment group and time point. Percent changes from baseline in LDL-C also were summarized by statin-tolerance subgroup. To assess the dose-response relationship for ETC-1002 monotherapy, the primary analysis of covariance model was used for the comparison of the ETC-1002 120 mg and ETC-1002 180 mg. Statistical testing of the efficacy endpoints was 2-sided and conducted at the 5% level of significance with no adjustment for multiple comparisons.

For the evaluation of safety, the incidence of AEs was summarized by system organ class and preferred term for each treatment group. Muscle-related AEs also were summarized by statin-tolerance subgroup. Actual values and changes from baseline in clinical laboratory parameters, vital sign measurements, electrocardiogram tracings, body weight, and ankle and waist circumference were summarized using descriptive statistics by treatment group and time point.

Figure 2:
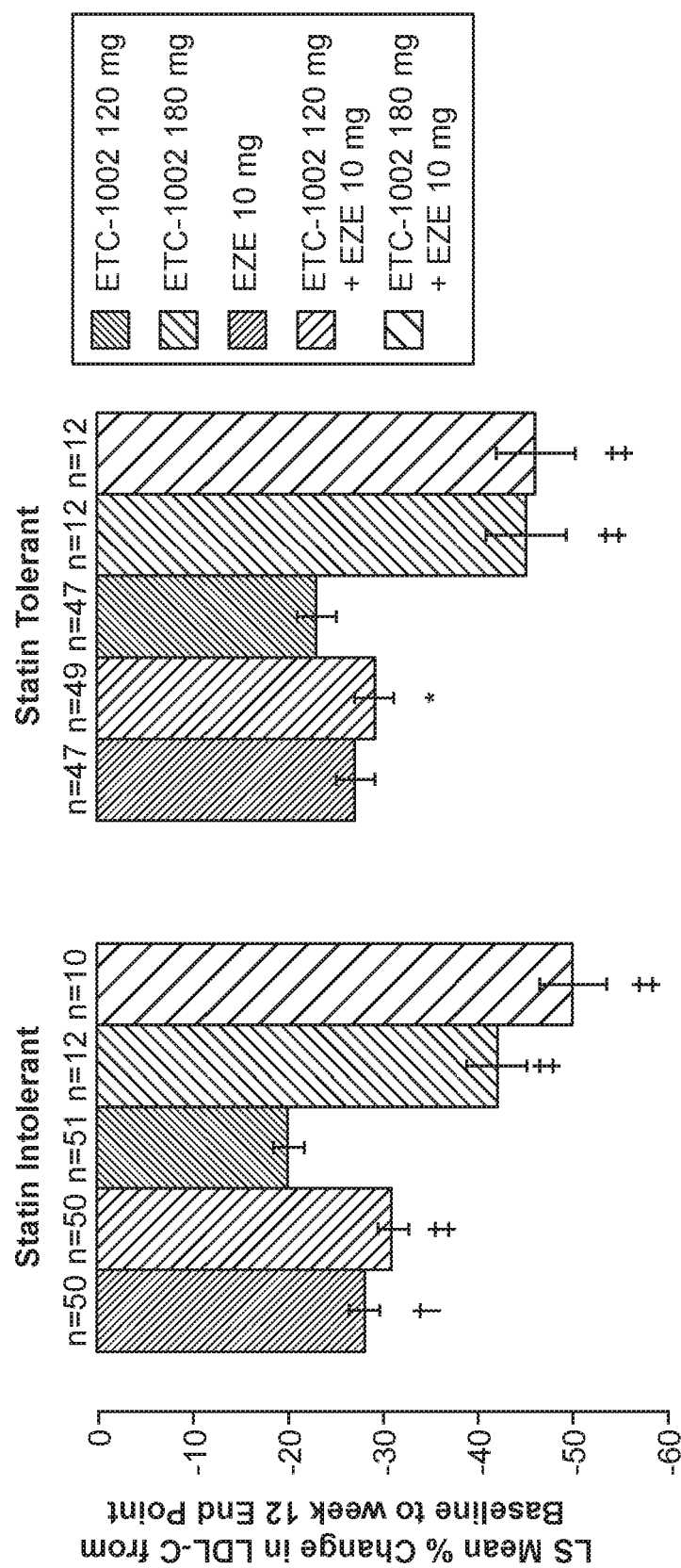
FIG. 2: Percent Changes from Baseline in LDL-C, Stratified by Statin Tolerance. Week 12 or last observation carried forward is the end-of-study endpoint and differs slightly from week 12 value; p-values versus EZE monotherapy were determined by an analysis of covariance model with terms for treatment and statin intolerance and baseline value as a covariate. *p≤0.05 versus EZE; †p≤0.01 versus EZE; ‡p<0.0001 versus EZE. EZE=Ezetimibe.
Figure 3:
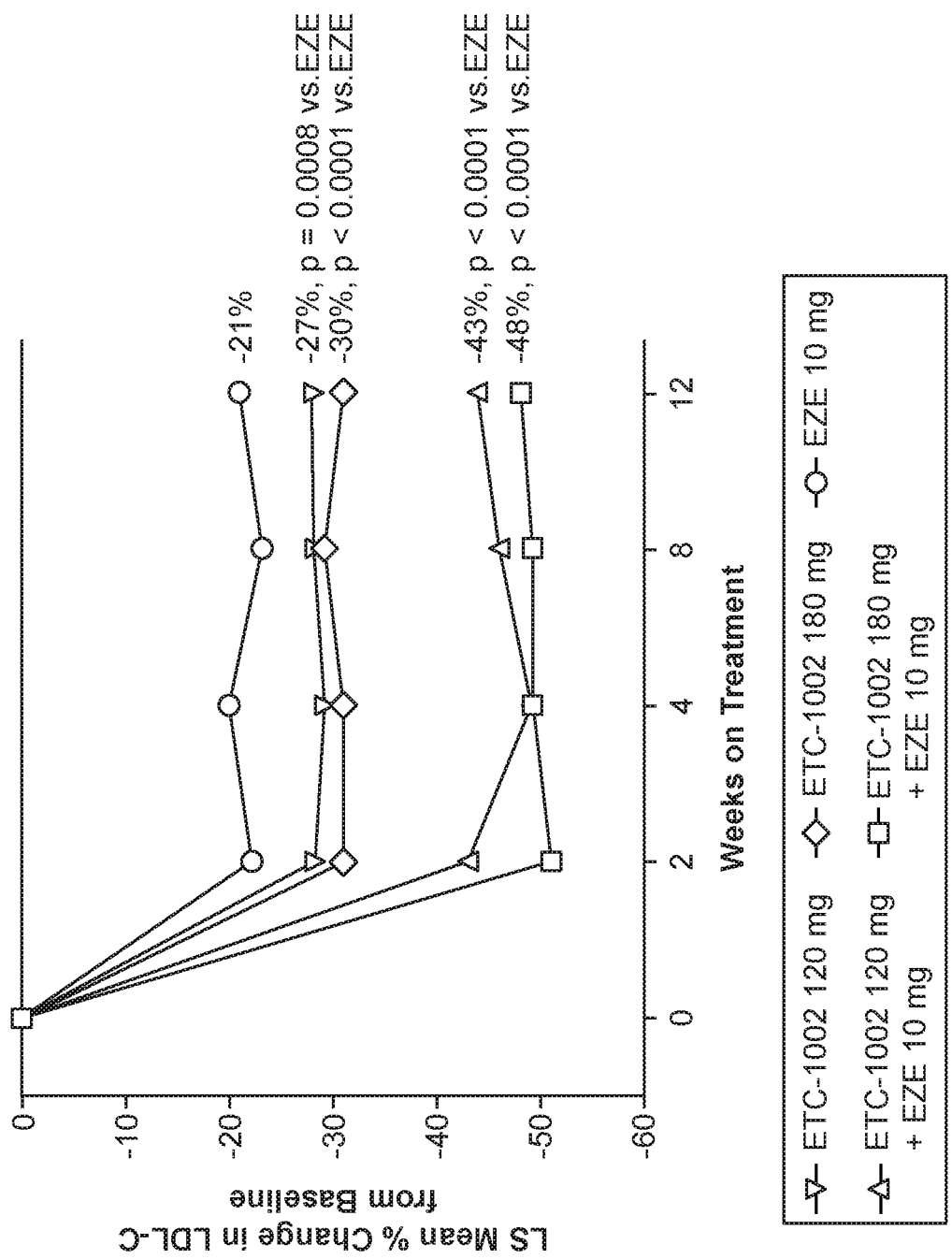
FIG. 3: Percent Changes from Baseline in LDL-C by Treatment Group and Time. P-values vs. EZE at week 12 endpoint are shown. Week 12 or last observation carried forward is the end-of-study endpoint and differs slightly from week 12 value; p-values versus EZE monotherapy were determined by an analysis of covariance model with terms for treatment and statin intolerance and baseline value as a covariate. EZE=Ezetimibe

Example 1: Etc-1002 Alone or in Combination with EZE Reduced LDL-C from Baseline to Week 12 More than EZE Monotherapy LDL-C reductions were greatest with the combination of ETC-1002 120 mg (43%) or 180 mg (48%) plus EZE (p<0.0001 vs. EZE alone, both comparisons) (Table 2). The combination treatment effect of ETC-1002 plus EZE was approximately equal to the sum of their individual effects on LDL-C. The LDL-C reduction was slightly, but not significantly, higher with ETC-1002 180 mg alone (30%) than with 120 mg alone (27%) (p=0.15). The percent reductions in LDL-C with ETC-1002 were similar in statin-intolerant and statin-tolerant patients (FIG. 2). LDL-C reductions were apparent and steady after 2 weeks of treatment (FIG. 3). ETC-1002 alone reduced LDL-C up to 30%, which was significantly greater than the reduction achieved with EZE monotherapy. The greatest mean reductions in LDL-C, which reached 43% and 48%, occurred with the combination of ETC-1002 120 mg or 180 mg with EZE, respectively. The decreases in LDL-C with ETC-1002, EZE, and the combination occurred within 2 weeks of treatment and were maintained throughout the study. LDL-C reductions in statin-intolerant patients appeared similar to those in statin-tolerant patients. This finding is noteworthy considering that statin-intolerant patients had a higher baseline risk for cardiovascular disease than statin-tolerant patients, with 28% versus 12% classified as "high" or "very high" risk per NCEP ATP III criteria, respectively.

Example 2: ETC-1002 Alone or with EZE Reduced LDL Particle Number, Apolipoprotein B, Total Cholesterol, and Non-HDL-C More than EZE Alone ETC-1002 alone or with EZE also reduced secondary lipid endpoints including non-HDL-C, total cholesterol, apolipoprotein B, and LDL particle number significantly more than EZE alone. HDL-C decreased with ETC-1002 treatment (by 3% to 6%) and increased with EZE alone (by 5%) (p<0.0001 to p<0.05 for ETC-1002 groups vs. EZE alone) (Table 2).

Example 3: Median Values for CRP Decreased from Baseline to the Week 12 Endpoint by 30% with ETC-1002 120 mg and 40% with ETC-1002 180 mg CRP reductions in the ETC-1002 monotherapy groups were significantly greater (p<0.01, both comparisons) than the 10% reduction observed with EZE alone (Table 2).

Example 4: ETC-1002 had a Modest Effect on Triglycerides and VLDL Particle Number Patients who were administered 120 mg and 180 mg ETC-1002 in combination with EZE had a reduction in triglycerides compared to patients administered ETC-1002 alone or EZE alone (Table 2). VLDL particle number decreased for patients administered 120 mg ETC-1002 and EZE although this effect was not less than the reduction of VLDL particle number in patients who were administered EZE alone.

Example 5: Apolipoprotein A-I is Altered in Patients Administered with ETC-1002 180 Mg Plus EZE Apoplioprotein A-1 was significantly decreased in patients who were administered 180 mg ETC-1002 in combination with EZE compared to patients administered EZE alone (Table 2).

Example 6: The Incidence of AEs in Each ETC-1002 Monotherapy Group was Similar to EZE Alone Most AEs were mild or moderate in severity. AEs deemed possibly, probably, or definitely related to study drug were least common with ETC-1002 120 mg and most frequent with ETC-1002 180 mg plus EZE. The frequency of AEs resulting in study discontinuation was similar between the ETC-1002 treatment groups and EZE. More statin-intolerant patients (n=17) experienced AEs resulting in discontinuation than did statin-tolerant patients (n=3). Four serious AEs were reported (Table 3), 3 of which were unrelated to study drug and did not result in discontinuation (hemothorax with ETC-1002 120 mg, pancreatitis relapse with ETC-1002 180 mg, and transient ischemic attack with EZE). One sudden death of unknown cause in a patient taking ETC-1002 120 mg was deemed possibly related to study drug as a temporal relationship could not be excluded.

Muscle AEs were less frequent and caused fewer discontinuations with ETC-1002 monotherapy than with EZE. In the entire study population, myalgia was the most common muscle-related AE, occurring in 3% of patients treated with ETC-1002 120 mg, 1% with ETC-1002 180 mg, 6% with EZE alone, 8% with ETC-1002 120 mg plus EZE, and 4% with ETC-1002 180 mg plus EZE. Muscle-related AEs were more common among statin-intolerant than statin-tolerant patients (Table 4). The most common muscle-related AE in statin-intolerant patients was myalgia, which was least frequent in the ETC-1002 monotherapy groups.

Overall, no clinically meaningful, dose-related trends in laboratory changes or abnormalities were observed. There also were no clinically meaningful changes in physical examination findings, vital sign measurements, ECG readings, weight, or waist or ankle circumference. Alanine aminotransferase or aspartate aminotransferase, or both, increased >3 times the upper limit of normal at any measurement in 1 patient treated with ETC-1002 120 mg, 2 patients with ETC-1002 180 mg, 1 patient with EZE, and 1 patient with ETC-1002 120 mg plus EZE. One patient treated with ETC-1002 120 mg plus EZE experienced a CK level >10 times the upper limit of normal, which occurred after heavy physical exertion and was accompanied by myalgia While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

Baseline Demographic and Clinical Characteristics

| | Safety Population | | | | | | |
|---|---|---|---|---|---|---|---|
| | Statin Intolerant n = 177 | Statin Tolerant n = 171 | ETC-1002 120 mg n = 99 | ETC-1002 180 mg n = 100 | EZE 10 mg n = 99 | ETC-1002 120 mg + EZE 10 mg n = 26 | ETC-1002 180 mg + EZE 10 mg n = 24 |
| Demographics | | | | | | | |
| Age, years | 62 ± 9 | 57 ± 9 | 61 ± 10 | 59 ± 9 | 60 ± 10 | 59 ± 10 | 59 ± 9 |
| Women | 57% | 47% | 54% | 51% | 52% | 54% | 54% |
| Caucasian | 89% | 91% | 91% | 91% | 88% | 92% | 92% |
| Not Hispanic/Latino | 94% | 84% | 92% | 85% | 90% | 92% | 92% |
| NCEP ATP III Risk Category Very High | 14% | 3% | 11% | 7% | 8% | 8% | 8% |
| NCEP ATP III Risk Category High | 14% | 9% | 14% | 10% | 11% | 12% | 8% |
| NCEP ATP III Risk Category Moderate | 41% | 50% | 38% | 49% | 49% | 42% | 46% |
| NCEP ATP III Risk Category Low | 32% | 38% | 36% | 34% | 32% | 39% | 38% |
| Clinical characteristics | | | | | | | |
| LDL-C, mg/dL | 169 ± 25 | 160 ± 25 | 164 ± 28 | 166 ± 24 | 165 ± 25 | 162 ± 26 | 162 ± 27 |
| Total cholesterol, mg/dL | 255 ± 33 | 244 ± 31 | 249 ± 31 | 253 ± 33 | 248 ± 32 | 247 ± 35 | 246 ± 32 |
| HDL-C, mg/dL | 53 ± 13 | 51 ± 15 | 54 ± 16 | 52 ± 13 | 49 ± 12 | 51 ± 15 | 52 ± 16 |
| Triglycerides, mg/dL* | 157 (52, 365) | 150 (38, 434) | 136 (71, 375) | 162 (38, 371) | 163 (64, 434) | 161 (81, 332) | 151 (50, 343) |
| CRP, mg/L*† | 1.90 (0.2, 31.7) | 2.20 (0.1, 22.5) | 1.60 (0.2, 19.2) | 2.50 (0.1, 20.3) | 2.60 (0.3, 31.7) | 1.85 (0.2, 19.5) | 1.25 (0.2, 4.7) |
| SBP, mmHg | 124 ± 11 | 126 ± 12 | 126 ± 11 | 125 ± 12 | 126 ± 12 | 126 ± 11 | 119 ± 12 |
| DBP, mmHg | 77 ± 8 | 78 ± 8 | 77 ± 8 | 78 ± 7 | 78 ± 7 | 77 ± 7 | 76 ± 9 |
| Weight, kg | 86 ± 17 | 88 ± 19 | 87 ± 18 | 89 ± 19 | 85 ± 17 | 88 ± 20 | 83 ± 22 |
| BMI, kg/m$^2$ | 30 ± 5 | 30 ± 5 | 31 ± 6 | 31 ± 5 | 30 ± 5 | 30 ± 5 | 28 ± 5 |

Values are mean ± SD or %, unless otherwise indicated. Baseline defined as the mean of the values from weeks −1 and 0, unless otherwise indicated.
*Median values (min, max).
†Baseline defined as the last value before the first dose of study drug.
BMI = body mass index;
DBP = diastolic blood pressure;
EZE = Ezetimibe;
HDL-C = high-density lipoprotein cholesterol;
CRP = high-sensitivity C-reactive protein;
LDL-C = low-density lipoprotein cholesterol;
NCEP ATPIII = National Cholesterol Education Program Adult Treatment Panel III;
SBP = systolic blood pressure.

TABLE 2

Percent Changes from Baseline to Week 12 in Lipids and CRP

| | mITT Population | | | | |
|---|---|---|---|---|---|
| | ETC-1002 120 mg n = 97 | ETC-1002 180 mg n = 99 | EZE 10 mg n = 98 | ETC-1002 120 mg + EZE 10 mg n = 24 | ETC-1002 180 mg + EZE 10 mg n = 22 |
| Primary endpoint | | | | | |
| LDL-C, mg/dL | −27.5 ± 1.3† | −30.1 ± 1.3* | −21.2 ± 1.3 | −43.1 ± 2.6* | −47.7 ± 2.8* |
| Secondary endpoints | | | | | |
| LDL particle number, nmol/L | −21.8 ± 1.7† | −24.6 ± 1.8* | −12.7 ± 1.7 | −35.0 ± 3.7* | −37.0 ± 3.6* |
| Apolipoprotein B, mg/dL | −19.3 ± 1.3‡ | −21.3 ± 1.3† | −15.2 ± 1.2 | −32.7 ± 2.7* | −35.2 ± 2.6* |
| Total cholesterol, mg/dL | −19.3 ± 0.9† | −20.7 ± 0.9* | −14.3 ± 0.9 | −30.6 ± 1.9* | −34.3 ± 2.0* |
| Non-HDL-C, mg/dL | −23.2 ± 1.2† | −25.3 ± 1.1* | −18.7 ± 1.2 | −37.4 ± 2.3* | −42.4 ± 2.4* |
| HDL-C, mg/dL | −5.8 ± 1.4* | −4.8 ± 1.4* | 5.0 ± 1.4 | −3.1 ± 2.8‡ | −3.7 ± 3.0† |
| HDL particle number, μmol/L | 5.0 ± 1.3 | 6.2 ± 1.4 | 6.7 ± 1.3 | 7.3 ± 2.9 | 5.1 ± 2.8 |

TABLE 2-continued

Percent Changes from Baseline to Week 12 in Lipids and CRP

| | mITT Population | | | | |
|---|---|---|---|---|---|
| | ETC-1002 120 mg n = 97 | ETC-1002 180 mg n = 99 | EZE 10 mg n = 98 | ETC-1002 120 mg + EZE 10 mg n = 24 | ETC-1002 180 mg + EZE 10 mg n = 22 |
| Apolipoprotein A-I, mg/dL | −0.2 ± 1.1 | 0.1 ± 1.2 | 2.0 ± 1.1 | −2.8 ± 2.4 | −4.1 ± 2.4‡ |
| Triglycerides, mg/dL§‖ | 0.0 (41.6) | −2.7 (46.2) | −7.0 (34.9) | −18.9 (25.5) | −12.2 (36.5) |
| VLDL particle number, nmol/L§ | −2.7 (68.5) | 15.3 (80.5) | −12.6 (63.4) | −11.7 (80.1) | 12.0 (78.1) |
| CRP, mg/L§‖¶ | −30.1 (55.4)† | −40.2 (53.3)† | −10.5 (59.0) | −38.1 (83.2) | −25.6 (37.2)‡ |

Values are least-squares mean ± SE, unless otherwise indicated,
*p < 0.0001;
†p ≤ 0.01;
‡p ≤ 0.05 versus EZE alone using an analysis of covariance model with terms for treatment and statin intolerance and baseline value as a covariate, unless otherwise indicated. Baseline defined as the mean of the values from weeks −1 and 0 unless otherwise indicated. Week 12 endpoint is the week 12 value or last observation carried forward.
§Median (interquartile range) values.
‖Non-parametric analysis versus EZE using Wilcoxon rank-sum test.
¶Baseline defined as the last value before the first dose of study drug.
CRP = high-sensitivity C-reactive protein; EZE = Ezetimibe; HDL-C = high-density lipoprotein cholesterol; LDL-C = low-density lipoprotein cholesterol; mITT = modified intent-to-treat; VLDL = very-low-density lipoprotein.

TABLE 3

Safety Overview: Treatment-Emergent Adverse Events

| | Safety Population | | | | |
|---|---|---|---|---|---|
| | ETC-1002 120 mg n = 99 | ETC-1002 180 mg n = 100 | EZE 10 mg n = 99 | ETC-1002 120 mg + EZE 10 mg n = 26 | ETC-1002 180 mg + EZE 10 mg n = 24 |
| Overview of AEs | | | | | |
| Any AE(s) | 50 (51%) | 55 (55%) | 53 (54%) | 14 (54%) | 17 (71%) |
| Serious AE(s)* | 2 (2%) | 1 (1%) | 1 (1%) | 0 | 0 |
| Study drug-related AE(s)† | 13 (13%) | 18 (18%) | 19 (19%) | 5 (19%) | 10 (42%) |
| Discontinuation due to AE(s) | 3 (3%) | 6 (6%) | 8 (8%) | 2 (8%) | 1 (4%) |
| Most common AEs‡ | | | | | |
| Constipation | 3 (3%) | 1 (1%) | 1 (1%) | 0 | 2 (8%) |
| Nasopharyngitis | 3 (3%) | 5 (5%) | 4 (4%) | 0 | 2 (8%) |
| Upper respiratory tract infection | 6 (6%) | 6 (6%) | 1 (1%) | 1 (4%) | 0 |
| Urinary tract infection | 0 | 4 (4%) | 6 (6%) | 0 | 1 (4%) |
| ALT increased | 0 | 0 | 1 (1%) | 2 (8%) | 0 |
| AST increased | 0 | 0 | 0 | 2 (8%) | 0 |
| Blood CK increased | 1 (1%) | 4 (4%) | 1 (1%) | 2 (8%) | 0 |
| Arthralgia | 4 (4%) | 1 (1%) | 4 (4%) | 2 (8%) | 1 (4%) |
| Back pain | 1 (1%) | 1 (1%) | 8 (8%) | 0 | 0 |
| Myalgia | 3 (3%) | 1 (1%) | 6 (6%) | 2 (8%) | 1 (4%) |
| Headache | 3 (3%) | 2 (2%) | 1 (1%) | 4 (15%) | 0 |

Values are n (%).
*Serious AEs included 3 patient with hemothorax and 1 patient with sudden death (ETC-1002 120 mg), pancreatitis relapse (ETC-1002 180 mg), and transient ischemic attack (EZE).
†AEs were categorized as drug related if relationship to study drug was deemed possible, probable, or definite, or if relationship to study drug was not recorded. The most common drug-related AEs were muscle spasms (3%), peripheral edema (2%), myalgia (2%), and muscle weakness (2%) with ETC-1002 120 mg; upper respiratory tract infection (2%), abnormal liver function test (2%), and pruritus (2%) with ETC-1002 180 mg; myalgia (6%), arthralgia (4%), and muscle spasms (3%) with EZE; and increased ALT (8%), increased AST (8%), and myalgia (8%) in the ETC-1002 120 mg plus EZE combination group. No drug-related AE was experienced by more than 1 patient treated with ETC-1002 180 mg plus EZE.
‡Most common AEs were those occurring in ≥ 5% patients/group.

AE = adverse event; ALT = alanine aminotransferase; AST = aspartate aminotransferase; CK = creatine kinase; EZE = Ezetimibe.

TABLE 4

Safety Overview: Muscle-Related Treatment-Emergent Adverse Events

| | Safety Population | | | | |
|---|---|---|---|---|---|
| | ETC-1002 120 mg | ETC-1002 180 mg | EZE 10 mg | ETC-1002 120 mg + EZE 10 mg | ETC-1002 180 mg + EZE 10 mg |
| Statin-Intolerant Patients | n = 51 | n = 51 | n = 51 | n = 12 | n = 12 |
| *Overview of Muscle-Related AEs* | | | | | |
| Any muscle-related AE | 7 (14%) | 6 (12%) | 9 (18%) | 2 (17%) | 2 (17%) |
| Leading to discontinuation | 1 (2%) | 2 (4%) | 5 (10%) | 0 | 0 |
| *Muscle-related AEs by MedDRA Preferred Term\** | | | | | |
| Muscle spasms | 3 (6%) | 2 (4%) | 1 (2%) | 0 | 0 |
| Muscular weakness | 2 (4%) | 1 (2%) | 1 (2%) | 0 | 0 |
| Musculoskeletal chest pain | 0 | 1 (2%) | 0 | 0 | 0 |
| Musculoskeletal stiffness | 0 | 0 | 1 (2%) | 0 | 0 |
| Myalgia | 2 (4%) | 1 (2%) | 6 (12%) | 2 (17%) | 1 (8%) |
| Pain in extremity | 1 (2%) | 1 (2%) | 3 (6%) | 0 | 1 (8%) |
| Sensation of heaviness | 0 | 0 | 1 (2%) | 0 | 0 |
| Statin-Tolerant Patients | n = 48 | n = 49 | n = 48 | n = 14 | n = 12 |
| *Overview of Muscle-Related Aes* | | | | | |
| Any muscle-related AE | 1 (2%) | 0 | 3 (6%) | 0 | 1 (8%) |
| Leading to discontinuation | 0 | 0 | 1 (2%) | 0 | 0 |
| *Muscle-Related AEs by MedDRA Preferred Term\** | | | | | |
| Muscle spasms | 0 | 0 | 2 (4%) | 0 | 1 (8%) |
| Musculoskeletal pain | 0 | 0 | 1 (2%) | 0 | 0 |
| Myalgia | 1 (2%) | 0 | 0 | 0 | 0 |

Values are n (%).

*Prespecified analysis of all Musculoskeletal and Connective Tissue Disorders AE terms except arthralgia, back pain, bone pain, bunion, bursitis, groin pain, intervertebral degeneration, intervertebral disc protrusion, joint stiffness, joint swelling, neck pain, osteoarthritis, plantar fasciitis, rotator cuff syndrome, and synovial cyst.

AE = adverse event; EZE = Ezetimibe; MedDRA = *Medical Dictionary for Regulatory Activities*, version 16.0.

REFERENCES CITED

1. Guyton J R, Bays H E, Grundy S M, Jacobson T A. An assessment by the Statin Intolerance Panel: 2014 update. J Clin Lipidol 2014; 8(Suppl 3):S72-S81.
2. I to M K, Maki K C, Brinton E A, et al. Muscle symptoms in statin users, associations with cytochrome P450, and membrane transporter inhibitor use: a subanalysis of the USAGE study. J Clin Lipid 2014; 8:69-76.
3. Parker B A, Capizzi J A, Grimaldi A S, et al. Effect of statins on skeletal muscle function. Circulation 2013; 127:96-103.
4. Stroes E S, Thompson P D, Corsini A, et al; European Atherosclerosis Society Consensus Panel. Statin-associated muscle symptoms: impact on statin therapy-European Atherosclerosis Society Consensus Panel Statement on Assessment, Aetiology and Management. Eur Heart J 2015; 36:1012-1022.
5. Mampuya W M, Frid D, Rocco M, et al. Treatment strategies in patients with statin intolerance: the Cleveland Clinic experience. Am Heart J 2013; 166:597-603.
6. Stone N J, Robinson J, Lichtenstein A H, et al. 2013 ACC/AHA Guideline on the Treatment of Blood Cholesterol to Reduce Atherosclerotic Cardiovascular Risk in Adults: a report of the American College of Cardiology/American Heart Association Task Force on Practice Guidelines. J Am Coll Cardiol 2014; 63(25 Pt B); 2889-2934.
7. Pinkosky S L, Filippov S, Srivastava R A, et al. AMP-activated protein kinase and ATP-citrate lyase are two distinct molecular targets for ETC-1002, a novel small molecule regulator of lipid and carbohydrate metabolism. J Lipid Res 2013; 54:134-51.
8. Filippov S, Pinkosky S L, Newton R S. LDL-cholesterol reduction in patients with hypercholesterolemia by modulation of adenosine triphosphate-citrate lyase and adenosine monophosphate-activated protein kinase. Curr Opin Lipidol 2014; 25:309-15.
9. Berkhout T A, Havekes L M, Pearce N J, Groot P H. The effect of (−)-hydroxycitrate on the activity of the low-density-lipoprotein receptor and 3-hydroxy-3-methylglutaryl-CoA reductase levels in the human hepatoma cell line Hep G2. Biochem J 1990; 272:181-6.
10. Ballantyne C M, Davidson M H, MacDougall D E, et al. Efficacy and safety of a novel dual modulator of adenosine triphosphate-citrate lyase and adenosine monophosphate-activated protein kinase in patients with hypercholesterolemia: results of a multicenter, randomized, double-blind, placebo-controlled, parallel-group trial. J Am Coll Cardiol 2013; 62:1154-62.
11. Gutierrez M J, Rosenberg N L, MacDougall D E, et al. Efficacy and safety of ETC-1002, a novel investigational low-density lipoprotein-cholesterol-lowering therapy for the treatment of patients with hypercholesterolemia and type 2 diabetes mellitus. Arterioscler Thromb Vasc Biol 2014; 34:676-83.
12. Thompson P D, Rubino J, Janik M J, et al. Use of ETC-1002 to treat hypercholesterolemia in patients with statin intolerance. J Clin Lipidol 2015 Mar. 19 [E-pub ahead of print]; http://dx.doi.org/10.1016/j.jacl.2015.03.003.
13. Ezetimibe (Zetia) [package insert]. Whitehouse Station, N J: Merck & Co., Inc.; 2013.
14. Rosenson R S, Baker S K, Jacobson T A, Kopecky S L, Parker B A. An assessment by the Statin Muscle Safety Task Force: 2014 update. J Clin Lipidol 2014; 8(Suppl 3):S58-S71.
15. Stein E A, Ballantyne C M, Windier E, et al. Efficacy and tolerability of fluvastatin X L 80 mg alone, Ezetimibe alone, and the combination of fluvastatin X L 80 mg with Ezetimibe in patients with a history of muscle-related side effects with other statins. Am J Cardiol 2008; 101:490-6.
16. Saougos V G, Tambaki A P, Kalogirou M, et al. Differential effect of hypolipidemic drugs on lipoprotein-associated phospholipase A2. Arterioscler Thromb Vasc Biol 2007; 27:2236-43.
17. Davidson M I-I, Dillon M A, Gordon B, et al. Colesevelam hydrochloride (cholestagel): a new, potent bile acid sequestrant associated with a low incidence of gastrointestinal side effects. Arch Intern Med 1999; 159: 1893-1900.
18. Knopp R H, Brown W V, Dujovne C A, et al. Effects of fenofibrate on plasma lipoproteins in hypercholesterolemia and combined hyperlipidemia. Am J Med 1987; 83:50-9.
19. Stroes E, Colquhoun D, Sullivan D, et al; GAUSS-2 Investigators. Anti-PCSK9 antibody effectively lowers cholesterol in patients with statin intolerance: the GAUSS-2 randomized, placebo-controlled phase 3 clinical trial of evolocumab. J Am Coll Cardiol 2014; 63:2541-8.
20. Moriarty P M, Thompson P D, Cannon C P, et al. ODYSSEY ALTERNATIVE: Efficacy and safety of the proprotein convertase subtilisin/kexin type 9 monoclonal antibody, alirocumab, versus Ezetimibe, in patients with statin intolerance as defined by a placebo run-in and statin rechallenge arm. Presented at: American Heart Association 2014 Scientific Sessions; Nov. 17, 2014; Chicago, Ill.
21. Kane J P. New horizons in lipid management. J Am Coll Cardiol 2013; 62:1163-4.

What is claimed:

1. A method of treating familial hypercholesterolemia in a subject in need thereof, the method comprising administering a fixed-dosed combination of 8-hydroxy-2,2,14,14-tetramethylpentadecanedioic acid and Ezetimibe to the subject, wherein the fixed-dose combination comprises a fixed 180 milligram (mg) dose of 8-hydroxy-2,2,14,14-tetramethylpentadecanedioic acid and a fixed 10 milligram (mg) dose of Ezetimibe.

2. The method of claim 1, wherein administering the fixed-dose combination decreases the level of LDL-C in the subject below that of a control subject receiving a placebo.

3. The method of claim 1, wherein administering the fixed-dose combination decreases the level of C-reactive protein (hsCRP) in the subject.

4. The method of claim 1, wherein administering the fixed-dose combination decreases the number of very low density lipoprotein in the subject.

5. The method of claim 1, wherein administering the fixed-dose combination reduces the risks of cardiovascular diseases in the subject.

6. The method of claim 1, wherein administering the fixed-dose combination decreases the level of LDL-C in the subject by at least 30% relative to baseline.

7. The method of claim 1, wherein administering the fixed-dose combination decreases the level of hsCRP in the subject by at least 26% relative to baseline.

8. The method of claim 1, wherein administering the fixed-dose combination decreases the level of hsCRP in the subject by at least 30% relative to baseline.

9. The method of claim 1, wherein the fixed-dose combination of 8-hydroxy-2,2,14,14-tetramethylpentadecanedioic acid and Ezetimibe is administered once daily to the subject.

10. The method of claim 1, wherein the fixed dose combination of 8-hydroxy-2,2,14,14-tetramethylpentadecanedioic acid and Ezetimibe is formulated to be a tablet.

11. The method of claim 1, wherein the fixed dose combination of 8-hydroxy-2,2,14,14-tetramethylpentadecanedioic acid and Ezetimibe is formulated for oral delivery.

12. The method of claim 1, wherein the fixed dose combination of 8-hydroxy-2,2,14,14-tetramethylpentadecanedioic acid and Ezetimibe is formulated for administration once daily.

13. The method of claim 1, wherein the subject is human.

* * * * *